(12) United States Patent
Wagner et al.

(10) Patent No.: US 7,772,242 B2
(45) Date of Patent: Aug. 10, 2010

(54) MEROCYANINE DERIVATIVES

(75) Inventors: Barbara Wagner, Lörrach (DE); Frank Bienewald, Hegenheim (FR); Heinz Wolleb, Fehren (CH); Olof Wallquist, Therwil (CH); Bernd Herzog, Grenzach-Wyhlen (DE); Thomas Ehlis, Freiburg (DE); Jürg Haase, Bettingen (CH)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 880 days.

(21) Appl. No.: 11/630,489

(22) PCT Filed: Jun. 20, 2005

(86) PCT No.: PCT/EP2005/052850

§ 371 (c)(1),
(2), (4) Date: Dec. 21, 2006

(87) PCT Pub. No.: WO2006/003094

PCT Pub. Date: Jan. 12, 2006

(65) Prior Publication Data

US 2009/0010860 A1    Jan. 8, 2009

(30) Foreign Application Priority Data

Jun. 29, 2004 (EP) ................... 04103018

(51) Int. Cl.
A61K 31/519 (2006.01)
A61K 31/445 (2006.01)
A61K 31/16 (2006.01)
A61K 31/165 (2006.01)

(52) U.S. Cl. ............ 514/258.1; 514/315; 514/579; 514/613

(58) Field of Classification Search ........ 514/258.1, 514/315, 579, 613
See application file for complete search history.

(56) References Cited

U.S. PATENT DOCUMENTS

| 4,457,911 | A | 7/1984 | Conner et al. ........... 424/59 |
| 5,380,700 | A | 1/1995 | Miyazaki et al. ......... 504/239 |
| 5,806,834 | A | 9/1998 | Yoshida ............... 252/589 |
| 2002/0187114 | A1 | 12/2002 | Mankovitz ........... 424/59 |
| 2004/0132796 | A1 | 7/2004 | Valla et al. ........... 514/408 |
| 2005/0255055 | A1 | 11/2005 | Wagner et al. ........ 424/59 |

FOREIGN PATENT DOCUMENTS

| DE | 947 185 | 8/1956 |
| DE | 102 40 863 | 3/2004 |

(Continued)

OTHER PUBLICATIONS

E. N. Dozorova et al., Translation of Khimiya Geterotsiklicheskikh Soedinenii, Vol. No. 8, pp. 1109-1114, (Aug. 1988).

Chiara B. Vicentini et al., Heterocycles, vol. 53, No. 6, pp. 1285-1292, (Feb. 2000).

Von Willi Kantlehner et al., Chemiker-Zeitung, vol. 114, No. 5, pp. 176-178, (1990).

*Primary Examiner*—Raymond J Henley, III
(74) *Attorney, Agent, or Firm*—Mervin G. Wood

(57) ABSTRACT

Disclosed is the use of the compounds of formula

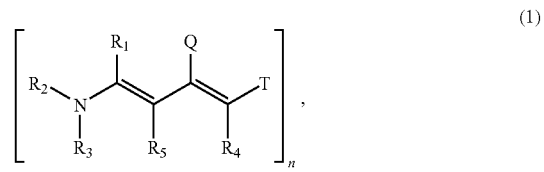

(1)

wherein

Q is —OH; —OR$_7$; —NH$_2$; —NHR$_7$; —NR$_7$R$_8$; or —N═R$_9$;

T is —COR$_5$; —CN; or —SO$_2$—(C$_6$-C$_{12}$)aryl;

R$_1$ is hydrogen; —OR$_7$, —SR$_7$; —NHR$_7$; —NR$_7$R$_8$; C$_1$-C$_{22}$alkyl; C$_2$-C$_{12}$Alkenyl; C$_2$-C$_{12}$alkinyl; C$_3$-C$_{12}$cycloalkyl; C$_3$-C$_{12}$cycloalkenyl; C$_7$-C$_{12}$aralkyl; C$_1$-C$_{12}$heteroalkyl, C$_2$-C$_{11}$heteroaralkyl; C$_6$-C$_{10}$aryl; or C$_1$-C$_9$heteroaryl;

R$_2$ and R$_3$ independently from each other are C$_1$-C$_{22}$alkyl; C$_2$-C$_{12}$alkenyl; C$_2$-C$_{12}$alkinyl; C$_3$-C$_{12}$cycloalkyl, C$_3$-C$_{12}$cycloalkenyl; C$_7$-C$_{12}$aralkyl; C$_1$-C$_{12}$heteroalkyl; C$_3$-C$_{12}$cycloheteroalkyl; C$_2$-C$_{11}$heteroaralkyl, C$_6$-C$_{10}$aryl; or C$_1$-C$_9$heteroaryl;

R$_4$ is cyano; COR$_7$, COOR$_7$; CONH$_2$; CONHR$_7$; CONR$_7$R$_8$; SO$_2$(C$_6$-C$_{12}$)aryl, C$_2$-C$_{12}$alk-1-enyl; C$_3$-C$_{12}$cycloalk-1-enyl; C$_2$-C$_{12}$alk-1-inyl; C$_2$-C$_{12}$cycloalk-1-inyl; C$_2$-C$_{12}$heteroalkyl, C$_3$-C$_5$heterocycloalkyl, C$_6$-C$_{10}$aryl; or C$_1$-C$_9$heteroaryl;

R$_5$ is —COR$_7$; —COOR$_7$; —OR$_7$; —SR$_7$, —NHR$_7$, —NR$_7$R$_8$; C$_1$-C$_{22}$alkyl; C$_2$-C$_{12}$alkenyl; C$_2$-C$_{12}$alkinyl; C$_3$-C$_{12}$cycloalkyl; C$_3$-C$_{12}$cycloalkenyl; C$_7$-C$_{12}$aralkyl; C$_1$-C$_{12}$alkylphenyl; C$_1$-C$_{12}$alkoxy-C$_6$-C$_{10}$aryl; C$_1$-C$_{12}$heteroalkyl; C$_2$-C$_{11}$heteroaralkyl; C$_3$-C$_{12}$cycloheteroalkyl; C$_6$-C$_{10}$aryl; C$_1$-C$_{12}$alkoxy-C$_6$-C$_{10}$aryl or C$_1$-C$_9$heteroaryl;

R$_6$, R$_7$ and R$_8$ independently from each other are hydrogen; C$_1$-C$_{22}$alkyl; C$_2$-C$_{12}$alkenyl; C$_2$-C$_{12}$alkinyl; C$_3$-C$_{12}$cycloalkyl; C$_3$-C$_{12}$cycloalkenyl; C$_7$-C$_{12}$aralkyl; C$_1$-C$_{12}$heteroalkyl; C$_2$-C$_{11}$heteroaralkyl; C$_6$-C$_{10}$aryl; o-C$_6$-C$_{10}$aryl; or C$_1$-C$_9$heteroaryl;

R$_9$ is a (C$_1$-C$_6$)alkylidene radical; or

R$_1$ and R$_2$, R$_1$ and Q, R$_1$ and R$_4$, R$_1$ and R$_6$, R$_2$ and R$_3$, R$_3$ and Q, R$_6$ and Q, T and Q, each independently, are linked together, so that 1, 2, 3 or 4 carbocyclic or N, O and/or S-heterocyclic rings are formed, wherein each of them, independently from each other, may be condensed with an aromatic or heteroaromatic ring, and/or more N-, O- and/or S-heterocycic rings, and each N atom in a N-heterocyclic ring may be substituted by C$_1$-C$_{22}$alkyl; and n is a number from 1 to 4;

for protecting of human hair and skin against the damaging effect of UV radiation.

27 Claims, No Drawings

FOREIGN PATENT DOCUMENTS

| | | |
|---|---|---|
| GB | 2 409 203 | 6/2005 |
| WO | 02/34710 | 5/2002 |
| WO | 03/068183 | 8/2003 |
| WO | 2004/006878 | 1/2004 |
| WO | 2005/012228 | 2/2005 |
| WO | 2005/080341 | 9/2005 |

MEROCYANINE DERIVATIVES

The present invention relates to the use of the compounds of formula

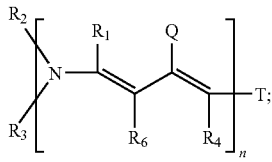

(1)

wherein

Q is hydrogen; $C_1$-$C_{22}$alkyl; —OH; —$OR_7$; —$NR_7R_8$; or —N=$R_9$;

$R_1$ is hydrogen; $C_1$-$C_{22}$alkyl; —$OR_7$; —$SR_7$; —$NR_7R_8$; $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; $C_7$-$C_{12}$aralkyl; $C_1$-$C_{12}$heteroalkyl, $C_2$-$C_{11}$heteroaralkyl; $C_6$-$C_{10}$aryl; or $C_1$-$C_9$heteroaryl;

$R_4$ is cyano; $COR_7$, $COOR_7$; $CONR_7R_8$; $SO_2(C_6$-$C_{12})$aryl; $C_2$-$C_{12}$alk-1-enyl; $C_3$-$C_{12}$cycloalk-1-enyl; $C_2$-$C_{12}$alk-1-inyl; $C_2$-$C_{12}$heteroalkyl; $C_3$-$C_5$heterocycloalkyl; $C_6$-$C_{10}$aryl; or $C_1$-$C_9$heteroaryl;

$R_5$ is —$COR_7$; —$COOR_7$; —$OR_7$; —$SR_7$, —$NHR_7$, —$NR_7R_8$; $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; $C_7$-$C_{12}$aralkyl; $C_1$-$C_{12}$alkylphenyl; $C_1$-$C_{12}$alkoxy-$C_6$-$C_{10}$aryl; $C_1$-$C_{12}$heteroalkyl; $C_2$-$C_{11}$heteroaralkyl; $C_3$-$C_{12}$cycloheteroalkyl; $C_6$-$C_{10}$aryl; $C_1$-$C_{12}$alkoxy-$C_6$-$C_{10}$aryl; or $C_1$-$C_9$heteroaryl;

$R_6$ is hydrogen; $C_1$-$C_{22}$alkyl; $C_1$-$C_{22}$alkoxy; or $COR_7$;

$R_7$ and $R_8$ independently from each other are hydrogen; $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; —$(CH_2)_t$COOH; $C_7$-$C_{12}$aralkyl; $C_1$-$C_{12}$heteroalkyl; $C_2$-$C_{11}$heteroaralkyl; $C_6$-$C_{10}$aryl; $C_1$-$C_9$heteroaryl; Si—$R_{10}R_{11}R_{12}$; Si$(OR_{10})(OR_{11})(OR_{12})$; Si$R_{10}(OR_{11})(OR_{12})$; Si$R_{10}R_{11}(OR_{12})$; —$(CH_2)_u$—O—$(CH_2)_v$—Si$R_{10}R_{11}R_{12}$; or a radical X-Sil;

t, u and v, independently from each other are a number from 1 to 5;

$R_9$ is a $(C_1$-$C_6)$alkylidene radical;

$R_{10}$, $R_{11}$, $R_{12}$ independently from each other are $C_1$-$C_{22}$alkyl;

X is a linker;

Sil is a silane-, oligosiloxane- or polysiloxane radical;

$R_1$ and $R_2$, $R_1$ and Q, $R_1$ and $R_6$, $R_1$ and T, $R_2$ and $R_3$, $R_2$ and $R_4$, $R_2$ and $R_6$, $R_2$ and Q, $R_4$ and $R_6$, $R_4$ and T, $R_6$ and Q, T and Q, each independently, are linked together, so that 1, 2, 3 or 4 carbocyclic or N, O and/or S-heterocylic rings are formed, wherein each of them, independently from each other, may be condensed with an aromatic or heteroaromatic ring, and/or more N-, O- and/or S-heterocyclic rings, and each N atom in a N-heterocyclic ring may be substituted by $C_1$-$C_{22}$alkyl;

n is a number from 1 to 4; wherein at least one of the radicals $R_1$, $R_6$ or Q is different from hydrogen;

if n=1

T is —$COR_5$; —CN; $C_6$-$C_{10}$aryl; —$NHR_5$; or —$SO_2$—$(C_6$-$C_{12})$aryl;

$R_2$ and $R_3$ independently from each other are $C_1$-$C_{22}$alkyl; hydroxy-$C_1$-$C_{22}$alkyl; $C_2$-$C_{12}$alkenyl; $C_2$-$C_{12}$alkinyl; $C_3$-$C_{12}$cycloalkyl, $C_3$-$C_{12}$cycloalkenyl; $C_7$-$C_{12}$aralkyl; $C_1$-$C_{12}$heteroalkyl; $C_3$-$C_{12}$cycloheteroalkyl; $C_6$-$C_{10}$aryl; $C_1$-$C_9$heteroaryl; or a radical of formula

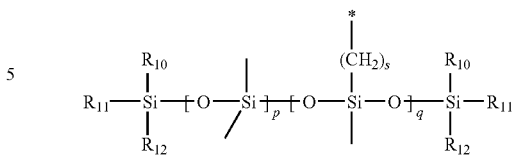

p is a number from 5 to 100
q is a number from 1 to 5;
s is a number from 0 to 4;
if n=2
$R_2$ and $R_3$ are each $C_1$-$C_5$alkylene; and simultaneously T is defined as for n=1; or
T is a bivalent radical of formula —$NR_7$—V—$NR_7$—, wherein
V is phenylene; or $C_1$-$C_5$alkylene;
$R_7$ is hydrogen; or $C_1$-$C_5$alkyl; and $R_2$ and $R_3$ simultaneously are defined as for n=1;
if n=3
one of $R_2$, $R_3$ or T is a trivalent radical;
if n=4
one of $R_2$, $R_3$ or T is a tetravalent radical;
for protecting of human hair and skin against the damaging effect of UV radiation.

Halogen ist chloro, bromo, fluoro or iodo, preferably chloro.

Alkyl, cycloalkyl, alkenyl, alkylidene or cycloalkenyl may be straight chained or branched, monocyclic or polycyclic.

Alkyl ist for example methyl, ethyl, n-propyl, isopropyl, n-butyl, sec.-butyl, isobutyl, tert-butyl, n-pentyl, 2-pentyl, 3-pentyl, 2,2-dimethylpropyl, n-hexyl, n-octyl, 1,1,3,3-tetramethylbutyl, 2-ethylhexyl, nonyl, decyl, n-octadecyl, eicosyl or dodecyl.

Alkenyl is for example straight-chain $C_2$-$C_{12}$alkenyl or preferably branched $C_3$-$C_{12}$alkenyl. $C_1$-$C_{12}$alkyl, like vinyl, allyl, 2-propen-2-yl, 2-buten-1-yl, 3buten-1-yl, 1,3-butadien-2-yl, 2-cyclobuten-1-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, 2-cyclopenten-1-yl, 2-cyclohexen-1-yl, 3-cyclohexen-1-yl, 2,4-cyclohexadien-1-yl, 1-p-menthen-8-yl, 4(10)-thujen-10-yl, 2-norbornen-1-yl, 2,5-norbornadien-1-yl, 7,7-dimethyl-2,4-norcaradien-3-yl oder die verschiedenen isomeren von hexenyl, octenyl, nonenyl, decenyl oder dodecenyl.

$C_3$-$C_{12}$-cycloalkyl is for example cyclopropyl, cyclobutyl, cyclopentyl, trimethylcyclohexyl or preferably cyclohexyl.

$C_7$-$C_{18}$aralkyl is for example benzyl, 2-benzyl-2-propyl, β-phenyl-ethyl, 9-fluorenyl, α,α,-di-methylbenzyl, ω-phenyl-butyl, ω-phenyl-octyl, ω-phenyl-dodecyl oder 3-methyl-5-(1',1',3',3'-tetramethyl-butyl)benzyl.

$(C_1$-$C_6)$alkylidene is for example methylene, ethyl-1-ene, propyl-2-ene. $C_6$-$C_{14}$ayrl is for example phenyl, naphthyl, biphenylyl, 2-fluorenyl, phenanthryl, anthracenyl or terphenylyl.

$C_1$-$C_{12}$heteroaryl is an unsaturated or aromatic radical having 4n+2 conjugated π-electrons, for example 2-thienyl, 2-furyl, 2-pyridyl, 2-thiazolyl, 2-oxazolyl, 2-imidazolyl, isothiazolyl, tri-azolyl, tetrazolyl or another ring system from thiophene-, furan-, pyridine, thiazol, oxazol, imidazol, isothiazol, triazol, pyridine- and benzene rings, which are unsubstituted or substituted by 1 to 6 ethyl, methyl, ethylene and/or methylene, like benzotriazolyl, bei N-heterocycles optionally in the form of their N-oxides.

$C_2$-$C_{16}$heteroaralkyl is for example $C_1$-$C_8$alkyl substituted with $C_1$-$C_8$heteroaryl.

Preferably compounds of formula (1) are used, wherein

Q is —OH; —OR$_7$; —NR$_7$R$_8$; or —N=R$_9$;

T is —COR$_5$; —CN; or —SO$_2$—($C_6$-$C_{12}$)aryl;

R$_1$ is hydrogen; —OR$_7$; —SR$_7$; —NR$_7$R$_8$; $C_1$-$C_{22}$alkyl; $C_2$-$C_{12}$alkenyl; $C_{12}$alkinyl; $C_3$-$C_{12}$cycloalkyl; $C_3$-$C_{12}$cycloalkenyl; $C_7$-$C_{12}$aralkyl; $C_1$-$C_{12}$heteroalkyl; $C_2$-$C_{11}$heteroaralkyl; $C_6$-$C_{10}$aryl; or $C_1$-$C_9$heteroaryl;

R$_2$ and R$_3$ independently from each other are $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; $C_7$-$C_{12}$aralkyl; $C_1$-$C_{12}$heteroalkyl; $C_3$-$C_{12}$cycloheteroalkyl; $C_2$-$C_{11}$heteroaralkyl, $C_6$-$C_{10}$aryl; or $C_1$-$C_9$heteroaryl;

R$_4$ is cyano; COR$_7$; COOR$_7$; CONR$_7$R$_8$; SO$_2$($C_6$-$C_{12}$)aryl; $C_2$-$C_{12}$alk-1-enyl; $C_3$-$C_{12}$cycloalk-1-enyl; $C_2$-$C_{12}$alk-1-inyl; $C_2$-$C_{12}$heteroalkyl, $C_3$-$C_5$heterocycloalkyl; $C_6$-$C_{10}$aryl; or $C_1$-$C_9$heteroaryl;

R$_5$ is —COR$_7$; —COOR$_7$; —OR$_7$; —SR$_7$; —NR$_7$R$_8$; $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; $C_7$-$C_{12}$aralkyl; $C_1$-$C_{12}$alkylphenyl; $C_1$-$C_{12}$alkoxy-$C_6$-$C_{10}$aryl; $C_1$-$C_{12}$heteroalkyl; $C_2$-$C_{11}$heteroaralkyl; $C_3$-$C_{12}$cycloheteroalkyl; $C_6$-$C_{10}$aryl; $C_1$-$C_{12}$alkoxy-$C_6$-$C_{10}$aryl or $C_1$-$C_9$heteroaryl;

R$_6$ is $C_1$-$C_{22}$alkyl; $C_1$-$C_{22}$alkoxy; or COR$_7$;

R$_7$ and R$_8$ independently from each other are hydrogen; $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; $C_7$-$C_{12}$aralkyl; $C_1$-$C_{12}$heteroalkyl; $C_2$-$C_{11}$heteroaralkyl; $C_6$-$C_{10}$aryl; o-$C_6$-$C_{10}$aryl; or $C_1$-$C_9$heteroaryl;

R$_9$ is a ($C_1$-$C_6$)alkylidene radical; or

R$_1$ and R$_2$, R$_1$ and Q, R$_1$ and R$_4$, R$_1$ and R$_6$, R$_2$ and R$_3$, R$_3$ and Q, R$_6$ and Q, T and Q, each independently, are linked together, so that 1, 2, 3 or 4 carbocyclic or N, O and/or S-heterocyclic rings are formed, wherein each of them, independently from each other, may be condensed with an aromatic or heteroaromatic ring, and/or more N-, O- and/or S-heterocycic rings, and each N atom in a N-heterocyclic ring may be substituted by $C_1$-$C_{22}$alkyl; and n is 1.

More preferred is the use of the compounds of formula (1), wherein

Q is —OH; —OR$_6$; or —NR$_7$R$_8$;

T is —COR$_5$ —CN; or —SO$_2$—($C_6$-$C_{12}$)aryl;

R$_1$ is hydrogen; —OR$_7$; —SR$_7$; —NR$_7$R$_8$; $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; $C_7$-$C_{12}$aralkyl; or $C_6$-$C_{10}$aryl;

R$_2$ and R$_3$ independently from each other are $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; $C_7$-$C_{12}$aralkyl; or $C_6$-$C_{10}$aryl;

R$_4$ is cyano; —COR$_5$, —COOR$_7$; —CONR$_7$R$_8$; —SO$_2$($C_6$-$C_{12}$)aryl; —$C_1$-$C_{22}$alkylcarbonylamino-$C_6$-$C_{10}$aryl; or $C_6$-$C_{10}$aryl;

R$_5$ is —COR$_7$; —COOR$_7$; —CONR$_7$R$_8$, —OR$_7$, —SR$_7$, —NR$_7$R$_8$, $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; $C_7$-$C_{12}$aralkyl; $C_6$-$C_{10}$aryl; or $C_1$-$C_{12}$alkoxy-$C_6$-$C_{10}$aryl;

R$_6$, R$_7$ and R$_8$ independently from each other are hydrogen; $C_1$-$C_{22}$alkyl; $C_3$-$C_{12}$cycloalkyl; $C_3$-$C_{12}$cycloalkenyl; $C_7$-$C_{12}$aralkyl; or $C_6$-$C_{10}$aryl; or R$_1$ and R$_2$, R$_1$ and Q, R$_1$ and R$_4$, R$_1$ and R$_6$, R$_2$ and R$_3$, R$_3$ and Q, R$_6$ and Q, T and Q are linked together pairwise, so that 1, 2, 3 or 4 carbocyclic or N-, O- and/or S-heterocyclic rings are formed, wherein each of them, independently from each other may be condensed with an aromatic or heteroaromatic ring, and/or more N, O and/or S-heterocyclic rings, and each N atom in a N-heterocyclic ring may be substituted by $C_1$-$C_{22}$alkyl.

Even more preferred is the use of the compounds of formula (1), wherein

R$_1$ is hydrogen; —S—$C_1$-$C_{22}$alkyl; or R$_1$ and R$_2$, or R$_1$ and R$_4$ together with the linking nitrogen atom form an alkylene radical which my be interrupted by one or more —O— and/or —NR$_7$— or may be condensed with an aromatic ring; and R$_7$ is $C_1$-$C_{22}$alkyl; $C_3$-$C_{12}$cycloalkyl; $C_3$-$C_{12}$cycloalkenyl; $C_7$-$C_{12}$aralkyl; or $C_6$-$C_{10}$aryl.

Most preferred is the use of the compounds of formula (1), wherein

R$_1$ is hydrogen.

Furthermore, the use of compounds formula (1) is preferred, wherein

R$_2$ and R$_3$ independently from each other are $C_1$-$C_5$alkyl; phenyl-$C_1$-$C_3$alkyl; hydroxy-$C_1$-$C_{12}$alkyl; or R$_2$ and R$_3$, or R$_2$ and R$_4$, or R$_2$ and Q together with the linking nitrogen atom form an alkylene radical which my be interrupted by one or more —O— and/or —NR$_7$— or may be condensed with an aromatic ring; and R$_7$ is $C_1$-$C_{22}$alkyl; $C_3$-$C_{12}$cycloalkyl; $C_3$-$C_{12}$cycloalkenyl; $C_7$-$C_{12}$aralkyl; or $C_6$-$C_{10}$aryl;

And most preferably the use of the compounds of formula (1), wherein

R$_2$ and R$_3$ independently from each other are $C_1$-$C_5$alkyl; or R$_2$ and R$_3$ together with the linking nitrogen atom form a $C_2$-$C_4$alkylene radical which may be interrupted by —O— or —NR$_7$; and R$_7$ is hydrogen; or $C_1$-$C_5$alkyl.

Preferred is also the use of compounds of formula (1), wherein

R$_4$ is —COR$_5$; phenyl, which is optionally substituted by $C_1$-$C_5$alkyl; —CN; or —SO$_2$—($C_6$-$C_{10}$)aryl; or R$_4$ and T together with a bivalent $C_3$-$C_7$alkylene radical which my be interrupted by one or more —O— and/or —NR$_7$— form a carbocyclic ring which may be condensed with an aromatic ring; and R$_7$ is hydrogen; or $C_1$-$C_5$alkyl.

Furthermore the use of compounds of formula (1) is preferred, wherein

R$_4$ is —CN; or COR$_5$;

R$_5$ is $C_1$-$C_{12}$alkyl; or $C_1$-$C_{12}$alkoxy; or

R$_4$ and T together with the bivalent radical of the formula

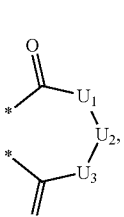

(1a)

wherein

U$_1$ and U$_3$ independently from each other are a radical of formula —CHR$_7$; —NHR$_7$—; or —O—;

U$_2$ is —CH$_2$; or —CO—; or the direct bond;

R$_7$ is hydrogen; or $C_1$-$C_{12}$alkyl; form an aromatic ring.

Most preferred is the use of compounds of formula (1), wherein

T and R₄ together with the bivalent radicals selected from

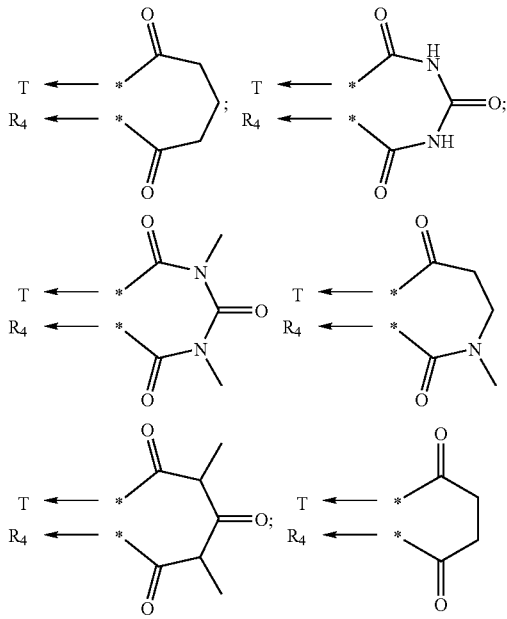

form a heterocyclic ring.

Furthermore, the use of compounds of formula (1) is preferred, wherein $R_6$ is hydrogen; $C_1$-$C_5$alkyl; $C_1$-$C_5$alkoxy; —O—($C_6$-$C_{10}$aryl); or $R_6$ and Q together with a bivalent $C_3$-$C_7$alkylene radical which may be interrupted by one or more —O— and/or —NR₇— or may be condensed with an aromatic ring, form a heterocyclic ring; and $R_7$ is hydrogen; or $C_1C_{12}$alkyl; and most preferably wherein $R_6$ is hydrogen.

Furthermore, the use of compounds ofse according to any of formula (1) is preferred, wherein T is —CN; —COR₅; or —SO₂-phenyl;

$R_5$ is $C_1$-$C_5$alkyl; $C_1$-$C_5$alkoxy; or NR₇R₈;

$R_7$ and $R_8$ independently from each other are hydrogen; or $C_1$-$C_5$alkyl; or T and Q together with the bivalent $C_3$-$C_7$alkylene radical which may be interrupted by one or more —O— and/or —NR₇— or may be condensed with an aromatic ring, form a heterocyclic ring; and most preferably the use of compounds of formula (1), wherein T is —CN; or —COR₅; and $R_5$ is $C_1$-$C_5$alkyl; or $C_1$-$C_6$alkoxy.

Furthermore, the use of compounds of formula (1) is preferred, wherein.

Q is hydroxy; $C_1$-$C_5$alkoxy; or —NR₇R₈; and $R_7$ and $R_8$ independently from each other are hydrogen; $C_1$-$C_5$alkyl; or phenyl, which may be substituted by one or more $C_1$-$C_5$alkyl or $C_1$-$C_5$alkoxy groups; and most preferably, wherein Q is hydroxy.

Furthermore, the use of compounds of formula

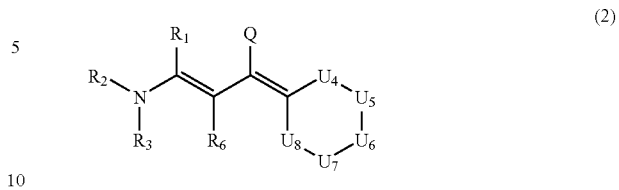

(2)

is preferred, wherein $U_4$, $U_5$, $U_6$, $U_7$ and $U_8$ independently of each other are —CHR₅—; —CO—; —NR₇—; —CS—; or —O—;

$R_5$ is hydrogen; or $C_1$-$C_5$alkyl; and $R_1$, $R_2$, $R_3$, $R_6$, $R_7$ and Q are defined as in formula (1).

Furthermore, the use of compounds of formula

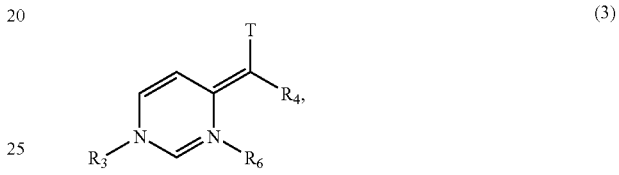

(3)

is preferred, wherein $R_5$ is hydrogen; or $C_1$-$C_5$alkyl; and $R_3$, $R_4$, and T are defined as in formula (1); more preferably, wherein $R_3$ is $C_1$-$C_{22}$alkyl; $C_6$-$C_{10}$aryl; or $C_7$-$C_{12}$aralkyl; and most preferably, wherein $R_3$ is $C_6$-$C_{10}$aryl.

Furthermore, the use of compounds of formula (1) is preferred, wherein at least one of the radicals $R_1$, $R_6$ or Q is different from hydrogen.

Preferred is also the use of compounds of formula (1), wherein

Q is hydrogen; or $C_1$-$C_{22}$alkyl;

T is —COR₅; —CN; or —SO₂—($C_6$-$C_{12}$)aryl;

$R_1$ is hydrogen; or $C_1$-$C_{22}$alkyl;

$R_2$ and $R_3$ independently from each other are $C_1$-$C_{22}$alkyl;

$R_4$ is CN; COR₅; CONH₂; or SO₂($C_6$-$C_{12}$)aryl, $R_5$ is —OR₇; —SR₇; —NHR₇; —NR₇R₈; $C_1$-$C_{22}$alkyl; $C_7$-$C_{12}$aralkyl;

$R_7$ and $R_8$ independently from each other are hydrogen; $C_1$-$C_{22}$alkyl; —(CH₂)$_m$—Si—R₁₀R₁₁R₁₂; Si(OR₁₀)(OR₁₁)(OR₁₂); SiR₁₀(OR₁₁)(OR₁₂); SiR₁₀R₁₁(OR₁₂), or a radical X-Sil;

$R_9$ is a ($C_1$-$C_6$)alkylidene radical;

$R_{10}$, $R_{11}$, $R_{12}$ independently from each other are $C_1$-$C_{22}$alkyl;

X is a linker;

Sil is a silane-, oligosiloxane- or polysiloxane radical;

$R_1$ and $R_2$, $R_1$ and Q, $R_1$ and $R_6$, $R_1$ and T, $R_2$ and $R_3$, $R_2$ and $R_4$, $R_2$ and $R_6$, $R_2$ and Q, $R_4$ and $R_6$, $R_4$ and T, $R_6$ and Q, T and Q, each independently, are linked together, so that 1, 2, 3 or 4 carbocyclic or N, O and/or S-heterocyclic rings are formed, wherein each of them, independently from each other, may be condensed with an aromatic or heteroaromatic ring, and/or more N-, O- and/or S-heterocycic rings, and each N atom in a N-heterocyclic ring may be substituted by $C_1$-$C_{22}$alkyl;

n is a number from 1 to 4; and m is a number for 0 to 4; wherein at least one of the radicals $R_1$, $R_6$ or Q is different from hydrogen;

Preferred is the use of compounds of formula (I), wherein
$R_1$, $R_6$ and Q, independently from each other are hydrogen; or $C_1$-$C_{22}$alkyl, wherein at least one of $R_1$, $R_6$ and Q is different from hydrogen; and most preferred the use of compounds of formula (1), wherein
$R_1$, $R_6$ and Q, independently from each other are hydrogen; or $C_1$-$C_5$alkyl, wherein at least one of $R_1$, $R_6$ and Q is different from hydrogen.

Preferred is also the use according of compounds of formula (I), wherein

T and $R_4$ independently from each other are —$COR_5$; —CN; or —$SO_2$—($C_6$-$C_{12}$)aryl; and $R_5$ is —$OR_7$; —$NR_7R_8$; $C_1$-$C_{22}$alkyl; $C_7$-$C_{12}$aralkyl;

$R_7$ and $R_8$ independently from each other are hydrogen; $C_1$-$C_{22}$alkyl; —$(CH_2)_m$—Si—$R_{10}R_{11}R_{12}$; and $R_{10}$, $R_{11}$, and $R_{12}$ independently from each other are $C_1$-$C_{22}$alkyl.

Most preferred is the use of compounds of formula (1), wherein T and $R_4$ independently from each other are —CN; $SO_2C_6H_5$;

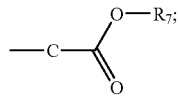

or a radical of formula

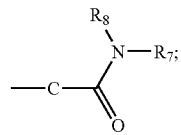

wherein
$R_7$ and $R_8$, independently from each other are $C_1$-$C_{12}$alkyl; or a radical of formula —$SiR_{10}R_{11}R_{12}$; and
$R_{10}$, $R_{11}$ and $R_{12}$ are $C_1$-$C_5$alkyl.

Furthermore the present invention relates to the use of monomeric and polymeric compounds having the structural element of formula

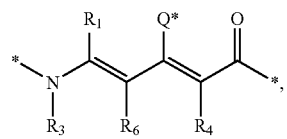

(4)

wherein at least one of the asterix-marked radicals are joint with the monomeric or polymeric radical; and
$R_1$, $R_2$, $R_4$ and $R_6$ are defined as in formula (1).

Examples of merocyanine derivatives used in the present invention are listed in Table 1:

TABLE MC2a
| | $R_2$ | $R_3$ | Q | $R_6$ | $R_1$ | T | $R_4$ |
|---|---|---|---|---|---|---|---|
| MC01 | i-propyl | 1-propyl | OH | H | H | | 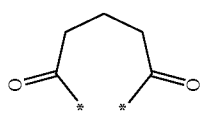 |
| MC02 $\lambda_{max}$ = 374 nm | $CH_3$ | $CH_3$ | OH | H | H | | |
| MC03 $\lambda_{max}$ = 375 nm | $CH_3$ | $CH_3$ | OH | H | H | | 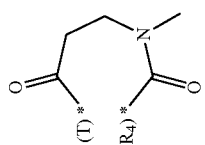 |
| MC04 $\lambda_{max}$ = 363 nm | $CH_3$ | $CH_3$ | OH | H | H | | 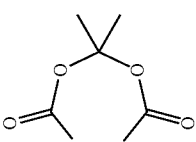 |

TABLE MC2a-continued
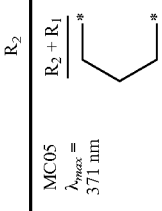
| | $R_2$ | $R_3$ | Q | $R_6$ | $R_1$ | T | $R_4$ |
|---|---|---|---|---|---|---|---|
| MC05 $\lambda_{max}$ = 371 nm | $R_2 + R_1$ 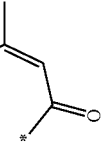 | $CH_3$ | OH | H | — | |  |
| MC06 $\lambda_{max}$ = 384 nm | $CH_3$ | $CH_3$ | OH | H | H | | |
| MC07 | 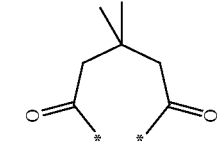 | | OH | H | H | | |
| MC08 | $CH_3$ | n-butyl | OH | H | H | | |

TABLE MC2a-continued

| | R₂ | R₃ | Q | R₆ | R₁ | T | R₄ |
|---|---|---|---|---|---|---|---|
| MC09 | CH₃ | CH₃ | OH | H | neopentyl-CH₂-S-* | —CN | *-(CO)-(CH₂)₂-(CO)-* |
| MC10 | CH₃ | CH₃ | OH | H | tetrahydrofuran-diyl | —(CO)—CH₃ | |
| MC11 | CH₃ | CH₃ | OH | H | H | 4-acetamidophenyl | 4-methoxybenzoyl |
| MC12 | oxepane-diyl (R₂-R₃) | | OH | H | H | 3-methylphenyl | ethoxyoxoacetyl |

TABLE MC2a-continued $$\underset{R_2}{\overset{R_1}{N}}\underset{R_3}{\overset{}{-}}\underset{R_6}{\overset{Q}{=}}\underset{R_4}{\overset{T}{=}}$$

| | $R_2$ | $R_3$ | Q | $R_6$ | $R_1$ | T | $R_4$ |
|---|---|---|---|---|---|---|---|
| MC13 | $R_2 + R_1$ <br> $\underset{}{O}-*(R_1)$ $*(R_2)$ | $CH_3$ | OH | H | — | —(CO)N($C_2H_5$)$_2$ | —(CO)—$CH_3$ |
| MC14 | $CH_3$ | $CH_3$ | OH | H | H | ![N with (T) and (R1)] | —(CO)—$CH_3$ |
| MC15 | ![cycloheptyl *—*] | | OH | H | H | ![phthaloyl] | |
| MC16 $\lambda_{max}$ = 399 nm | $CH_3$ | $CH_3$ | OH | H | H | ![diethyl thiourea diacyl] | |

TABLE MC2a-continued

![structure: R2-N(R3)-C(R1)=C(R6)-C(Q)(T)=C(R4)]

| | $R_2$ | $R_3$ | Q | $R_6$ | $R_1$ | T | $R_4$ |
|---|---|---|---|---|---|---|---|
| MC17 $\lambda_{max}$ = 373 nm | —CH$_3$ | i-propyl | OH | H | H | | (3,3-dimethylglutaryl diketone linker) |
| MC18 | i-propyl | i-propyl | OH | H | H | | (3,3-dimethylglutaryl diketone linker) |
| MC19 $\lambda_{max}$ = 380 nm | CH$_3$ | CH$_3$ | OH | CH$_3$ | H | | (N,N'-dimethylmalonyl diamide linker) |
| MC20 $\lambda_{max}$ = 368 nm | CH$_3$ | CH$_3$ | OH | H | H | | (ester-ketone linker) |
| MC21 | CH$_3$ | CH$_3$ | —O—C$_6$H$_5$ | H | H | —(CO)—CH$_3$ | CN |

TABLE MC2a-continued

| | $R_2$ | $R_3$ | Q | $R_6$ | $R_1$ | T | $R_4$ |
|---|---|---|---|---|---|---|---|
| MC22 | CH$_3$ | CH$_3$ | —O—CH$_3$ | H | H | —(CO)—O—CH$_3$ | CN |
| MC23 | $R_2 + R_1$: cyclohexane (*R$_1$, *R$_2$) | C$_2$H$_5$ | —OC$_2$H$_5$ | H | — | (neopentyl group) | —(CO)OCH$_3$ |
| MC24 | $R_2 + R_1$: phenyl with O—*(R$_1$), *(R$_2$) | C$_2$H$_5$ | —OC$_2$H$_5$ | | — | —(CO)OC$_2$H$_5$ | —(CO)OC$_2$H$_5$ |
| MC25 | CH$_3$ | CH$_3$ | O—*(Q), *(R$_6$) dioxolane | | H | —CO—O—C$_2$H$_5$ | —CN |
| MC26 | CH$_3$ | CH$_3$ | Q + T: methyl pyranone (*(Q), *(T)) | H | H | — | —(CO)OC$_2$H$_5$ |
| MC27 | CH$_3$ | CH$_3$ | Q + R$_1$: O—*(Q), *(R$_1$) | H | — | —(CO)—O—CH$_3$ | —CN |

TABLE MC2a-continued
| | $R_2$ | $R_3$ | Q | $R_6$ | $R_1$ | T | $R_4$ |
|---|---|---|---|---|---|---|---|
| MC28 | $CH_3$ | $CH_3$ | $Q + R_1$:  | H | — | $-(CO)-O-CH_3$ | $-SO_2-C_6H_5$ |
| MC29 $\lambda_{max}$ = 321 nm | $CH_3$ | $CH_3$ | $-N(CH_3)_2$ | H | H | $-(CO)-CH_3$ | $-(CO)OC_2H_5$ |
| MC30 | $CH_3$ | $CH_3$ | $-N(CH_3)_2$ | H | H | $-CN$ | $-(CO)-OCH_3$ |
| MC31 $\lambda_{max}$ = 321 nm | $CH_3$ | $CH_3$ | $-N(CH_3)_2$ | H | H | $-(CO)OC_2H_5$ | $-(CO)OC_2H_5$ |
| MC32 | $CH_3$ | $CH_3$ | $-NH_2$ | H | H | $-CN$ | $-(CO)OC_2H_5$ |
| MC33 | $CH_3$ | $CH_3$ |  | H | H | $-CN$ | $-(CO)OC_2H_5$ |
| MC34 | $CH_3$ | $CH_3$ | $R_6 + Q$:  | | H | $-CN$ | $-(CO)OC_2H_5$ |

TABLE MC2a-continued

![structure: R1-N(R2)(R3) attached to C=C(R6)-C(Q)=C(T)(R4)]

| | R$_2$ | R$_3$ | Q | R$_6$ | R$_1$ | T | R$_4$ |
|---|---|---|---|---|---|---|---|
| MC35 | CH$_3$ | CH$_3$ | R$_6$ + Q: [pyrrolidine-type ring (Q)*–N–(R$_6$)*] | H | H | —CN | —(CO)OC$_2$H$_5$ |
| MC36 | R$_2$ + Q: [*(Q)–NH–CH(R$_2$)*–CH$_3$] | CH$_3$ | — | H | H | —CN | —(CO)OC$_2$H$_5$ |
| MC37 | R$_2$ + Q: [*(Q)–N(H)–CH$_2$*(R$_2$)] | benzyl (–CH$_2$–C$_6$H$_5$*) | — | H | H | —CN | —(CO)OC$_2$H$_5$ |
| MC38 | R$_2$ + Q: [*(Q)–N=CH*(R$_2$)] | phenyl (–C$_6$H$_5$*) | — | H | H | —CN | —(CO)OC$_2$H$_5$ |
| MC39 | R$_2$ + Q: [*(Q)–N=CH*(R$_2$)] | CH$_3$ | — | H | H | —CN | 2-ethylhexyl ester (–C(=O)O–CH$_2$–CH(C$_2$H$_5$)–C$_4$H$_9$)* |

TABLE MC2a-continued

| | $R_2$ | $R_3$ | Q | $R_6$ | $R_1$ | T | $R_4$ |
|---|---|---|---|---|---|---|---|
| MC40 | $R_2$+Q: N=CH (Q)(R_2) | 2-ethylhexyl | — | H | H | —CN | —(CO)—O—$C_2H_5$ |
| MC41 | $CH_3$ | $CH_3$ | OH | H | H | — | (diacetyl imide structure) |
| MC42 | $CH_3$ | $CH_3$ | Q+T: cyclic urea | H | H | — | — |
| MC43 | $R_2$+Q: N=CH (Q)(R_2) | HO-CH_2CH_2CH_2-* | — | H | H | —CN | —(CO)—O—$C_2H_5$ |

TABLE MC2a-continued
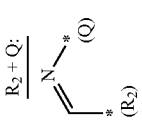
| | $R_2$ | $R_3$ | Q | $R_6$ | $R_1$ | T | $R_4$ |
|---|---|---|---|---|---|---|---|
| MC44 | $R_2+Q$: 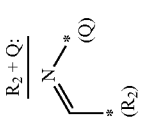 | $CH_3$ | — | H | H | —(CO)—O—$C_2H_5$ | —(CO)—O—$C_2H_5$ |
| MC45 $\lambda_{max}=$ 364 nm | $R_2+Q$: 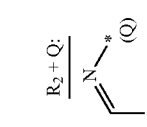 | 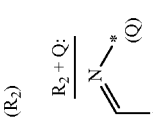 | — | H | H | —CN | —(CO)—O—$C_2H_5$ |
| MC46 | $R_2+Q$: 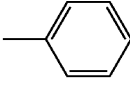 | H | — | H | H | —CN | —(CO)—O—$C_2H_5$ |
| MC47 | $R_2+Q$: 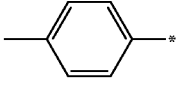 | 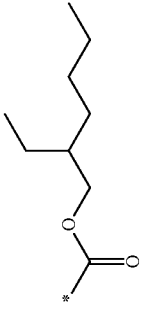 | — | H | H | —CN | (2-ethylhexyl ester structure) |

TABLE MC2a-continued

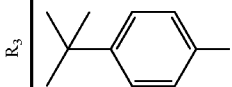

| | $R_2$ | $R_3$ | Q | $R_6$ | $R_1$ | T | $R_4$ |
|---|---|---|---|---|---|---|---|
| MC48 | $\dfrac{R_2 + Q:}{\overset{*}{N}=\overset{*}{\underset{(R_2)}{\text{(Q)}}}}$ | | — | H | H | —CN | —(CO)—O—C$_2$H$_5$ |
| MC49 | CH$_3$ | CH$_3$ | OH | H | H | (hydantoin ring) | |
| MC50 | CH$_3$ | CH$_3$ | CH$_3$ | H | H | —COOCH$_3$ | —COOCH$_3$ |
| MC51 | CH$_3$ | CH$_3$ | CH$_3$ | H | H | —COOC$_2$H$_5$ | —COOC$_2$H$_5$ |
| MC52 | CH$_3$ | CH$_3$ | CH$_3$ | H | H | —COOC$_3$H$_7$-(n) | —COOC$_3$H$_7$-(n) |
| MC53 | CH$_3$ | CH$_3$ | CH$_3$ | H | H | —COOC$_3$H$_7$-(i) | —COOC$_3$H$_7$-(i) |
| MC54 | CH$_3$ | CH$_3$ | CH$_3$ | H | H | —COOC$_4$H$_9$-(n) | —COOC$_4$H$_9$-(n) |
| MC55 | CH$_3$ | CH$_3$ | CH$_3$ | H | H | —COOC$_4$H$_9$-(t) | —COOC$_4$H$_9$-(t) |
| MC56 | CH$_3$ | CH$_3$ | CH$_3$ | H | H | —COOC$_4$H$_9$-(t) | —COOC$_4$H$_9$-(t) |
| MC57 | CH$_3$ | CH$_3$ | CH$_3$ | H | H | —COOCH$_3$ | —COOCH$_3$ |
| MC58 | CH$_3$ | CH$_3$ | CH$_3$ | H | H | —COOC$_2$H$_5$ | —COOSi(CH$_3$)$_3$ |
| MC59 | CH$_3$ | CH$_3$ | CH$_3$ | H | H | —COOSi(CH$_3$)$_3$ | —COOSi(CH$_3$)$_3$ |
| MC60 | CH$_3$ | CH$_3$ | CH$_3$ | H | H | —CO$_2$(CH$_2$)$_3$Si(CH$_3$)$_3$ | —CO$_2$(CH$_2$)$_3$Si(CH$_3$)$_3$ |
| MC61 | CH$_3$ | CH$_3$ | CH$_3$ | H | H | —CONHC$_2$H$_5$ | —CONHC$_2$H$_5$ |
| MC62 | CH$_3$ | CH$_3$ | CH$_3$ | H | H | —CON(C$_2$H$_5$)$_2$ | —CON(C$_2$H$_5$)$_2$ |
| MC63 | CH$_3$ | CH$_3$ | CH$_3$ | H | H | CN | CN |
| MC64 | CH$_3$ | CH$_3$ | CH$_3$ | H | H | CN | SO$_2$C$_6$H$_6$ |
| MC65 | CH$_3$ | CH$_3$ | CH$_3$ | H | H | CN | COOC$_4$H$_9$-(i) |
| MC66 | CH$_3$ | CH$_3$ | CH$_3$ | H | H | CN | COOC$_8$H$_{17}$-(i) |
| MC67 | CH$_3$ | CH$_3$ | CH$_3$ | H | H | CN | COOCH$_3$ |
| MC68 | CH$_3$ | CH$_3$ | CH$_3$ | H | H | CN | COOC$_2$H$_5$ |
| MC69 | CH$_3$ | CH$_3$ | CH$_3$ | H | H | CN | —CONHC$_2$H$_5$ |
| MC70 | CH$_3$ | CH$_3$ | CH$_3$ | H | H | CN | —CON(C$_2$H$_5$)$_2$ |
| MC71 | CH$_3$ | CH$_3$ | CH$_3$ | H | H | SO$_2$C$_6$H$_6$ | COOCH$_3$ |

TABLE MC2a-continued

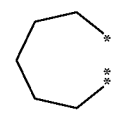

| | R2 | R3 | Q | R6 | R1 | T | R4 |
|---|---|---|---|---|---|---|---|
| MC72 | CH3 | CH3 | CH3 | H | H | SO2C6H6 | COOC2H5 |
| MC73 | CH3 | CH3 | CH3 | H | H | SO2C6H6 | COOC3H7 |
| MC74 | CH3 | CH3 | CH3 | H | H | SO2C6H6 | COOC4H9 |
| MC75 | CH3 | CH3 | CH3 | H | H | SO2C6H6 | COOC8H17(n) |
| MC76 | CH3 | CH3 | CH3 | H | H | SO2C6H6 | COOC8H17(i) |
| MC77 | CH3 | CH3 | CH3 | H | H | SO2C6H6 | —CONHC2H5 |
| MC78 | CH3 | CH3 | CH3 | H | H | SO2tolyl | —COOC2H5 |
| MC79 | CH3 | CH3 | CH3 | H | CH3 | —COOCH3 | —COOCH3 |
| MC80 | CH3 | CH3 | CH3 | H | CH3 | —COOC2H5 | —COOC2H5 |
| MC81 | CH3 | CH3 | CH3 | H | CH3 | —COOC3H7-(n) | —COOC3H7-(n) |
| MC82 | CH3 | CH3 | CH3 | H | CH3 | —COOC3H7-(i) | —COOC3H7-(i) |
| MC83 | CH3 | CH3 | CH3 | H | CH3 | —COOC4H9-(n) | —COOC4H9-(n) |
| MC84 | CH3 | CH3 | CH3 | H | CH3 | —COOC4H9-(t) | —COOC4H9-(t) |
| MC85 | CH3 | CH3 | CH3 | H | CH3 | —COOC2H5 | —COOC2H5 |
| MC86 | CH3 | CH3 | CH3 | H | CH3 | —COOC2H5 | —COOSi(CH3)3 |
| MC87 | CH3 | CH3 | CH3 | H | CH3 | —COOSi(CH3)3 | —COOSi(CH3)3 |
| MC88 | CH3 | CH3 | CH3 | H | CH3 | —CONHC2H5 | —CONHC2H5 |
| MC89 | CH3 | CH3 | CH3 | H | CH3 | —CON(C2H5)2 | —CON(C2H5)2 |
| MC90 | CH3 | CH3 | CH3 | H | CH3 | CN | CN |
| MC91 | CH3 | CH3 | CH3 | H | CH3 | CN | SO2C6H6 |
| MC92 | CH3 | CH3 | CH3 | H | CH3 | CN | COOC4H9-(n) |
| MC93 | CH3 | CH3 | CH3 | H | CH3 | CN | COOC8H17(i) |
| MC94 | CH3 | CH3 | CH3 | H | CH3 | CN | COOCH3 |
| MC95 | CH3 | CH3 | CH3 | H | CH3 | CN | COOC2H5 |
| MC96 | CH3 | CH3 | CH3 | H | CH3 | CN | —CONHC2H5 |
| MC97 | CH3 | CH3 | CH3 | H | CH3 | CN | —CON(C2H5)2 |
| MC98 | CH3 | CH3 | CH3 | H | CH3 | CN | COOCH3 |
| MC99 | CH3 | CH3 | CH3 | H | CH3 | CN | COOC2H5 |
| MC100 | CH3 | CH3 | CH3 | H | CH3 | SO2C6H6 | COOC3H7 |
| MC101 | CH3 | CH3 | CH3 | H | CH3 | SO2C6H6 | COOC4H9 |
| MC102 | CH3 | CH3 | CH3 | H | CH3 | SO2C6H6 | COOC8H17(n) |
| MC103 | CH3 | CH3 | CH3 | H | CH3 | SO2C6H6 | COOC8H17(i) |
| MC104 | CH3 | CH3 | CH3 | H | CH3 | SO2C6H6 | —COOC2H5 |
| MC105 | CH3 | CH3 | CH3 | H | CH3 | SO2C6H6 | —CONHC2H5 |
| MC106 | CH3 | CH3 | CH3 | H | CH3 | SO2tolyl | —COOC2H5 |
| MC107 | CH3 | CH3 | CH3 | H | CH3 | SO2tolyl | —COOCH3 |
| MC108 | CH3 | CH3 | CH3 | H | H | —COOC2H5 | —COOC2H5 |
| MC109 | CH3 | CH3 | CH3 | H | H | —COOSi(CH3)3 | —COOSi(CH3)3 |
| MC110 | CH3 | CH3 | CH3 | H | H | CN | CN |
| MC111 | CH3 | CH3 | CH3 | H | H | CN | COOC2H5 |
| MC112 | CH3 | CH3 | CH3 | H | H | CN | COOCH3 |
| MC113 | CH3 | CH3 | CH3 | H | H | SO2C6H6 | COOCH3 |

For MC108–MC113, R2 and R3 together form a seven-membered ring:

TABLE MC2a-continued

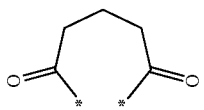 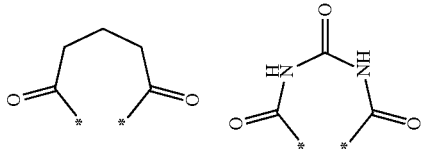

| | $R_2$ | $R_3$ | Q | $R_6$ | $R_1$ | T | $R_4$ |
|---|---|---|---|---|---|---|---|
| MC114 | | | $CH_3$ | H | H | $SO_2$tolyl | $COOC_2H_5$ |
| MC115 | | | $CH_3$ | H | $CH_3$ | $-COOC_2H_5$ | $-COOC_2H_5$ |
| MC116 | | | $CH_3$ | H | $CH_3$ | $-COOSi(CH_3)_3$ | $-COOSi(CH_3)_3$ |
| MC117 | | | $CH_3$ | H | $CH_3$ | CN | CN |
| MC118 | | | $CH_3$ | H | $CH_3$ | CN | $SO_2C_6H_6$ |
| MC119 | | | $CH_3$ | H | $CH_3$ | CN | $COOC_8H_{17}$-(i) |
| MC120 | 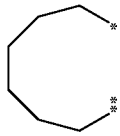 | | $CH_3$ | H | H | $SO_2C_6H_6$ | $COOCH_3$ |
| MC121 | | | $CH_3$ | H | H | $-COOC_2H_5$ | $-COOC_2H_5$ |
| MC122 | | | $CH_3$ | H | H | $-COOSi(CH_3)_3$ | $-COOSi(CH_3)_3$ |
| MC123 | | | $CH_3$ | H | H | CN | CN |
| MC124 | | | $CH_3$ | H | $CH_3$ | CN | $SO_2C_6H_6$ |
| MC125 | | | $CH_3$ | H | $CH_3$ | CN | $COOC_8H_{17}$-(i) |
| MC126 | | | $CH_3$ | H | $CH_3$ | $SO_2C_6H_6$ | $COOCH_3$ |
| MC127 | | | $CH_3$ | H | $CH_3$ | $-COOC_2H_5$ | $-COOC_2H_5$ |
| MC128 | | | $CH_3$ | H | $CH_3$ | $-COOSi(CH_3)_3$ | $-COOSi(CH_3)_3$ |
| MC129 | | | $CH_3$ | H | $CH_3$ | CN | CN |
| MC130 | | | $CH_3$ | H | $CH_3$ | CN | $SO_2C_6H_6$ |
| MC131 | | | $CH_3$ | H | $CH_3$ | CN | $COOC_8H_{17}$-(i) |
| MC132 | | | $CH_3$ | H | $CH_3$ | $SO_2$tolyl | $COOCH_3$ |
| MC133 | | | $CH_3$ | H | $CH_3$ | $SO_2$tolyl | $-CONHC_2H_5$ |
| MC134 | i-propyl | i-propyl | $CH_3$ | H | H | 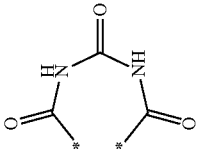 | |
| MC135 | $CH_3$ | $CH_3$ | $CH_3$ | | H | | |

TABLE MC2a-continued

| | R₂ | R₃ | Q | R₆ | R₁ | T | R₄ |
|---|---|---|---|---|---|---|---|
| MC136 | CH₃ | CH₃ | CH₃ | H | H | | (acetyl-N(CH₃)-acetyl group) |
| MC137 | (R₂+R₁ propylene linker) | (piperidine ring) | CH₃ | H | H | | (acetonide group) |
| MC138 | (R₂+R₁ propylene linker) | CH₃ | CH₃ | H | — | | (N,N'-dimethyl dicarbonyl group) |
| MC139 | CH₃ | H | CH₃ | H | CH₃ | —(CO)OCH₃ | —(CO)OCH₃ |
| MC140 | (R₂+R₃ hexamethylene linker forming azocane) | | H | CH₃ | H | | (2,4-dimethyl-3-oxoglutaryl group) |

TABLE MC2a-continued

| | $R_2$ | $R_3$ | Q | $R_6$ | $R_1$ | T | $R_4$ |
|---|---|---|---|---|---|---|---|
| MC141 | $CH_3$ | $n-C_4H_9$ | $CH_3$ | H | $CH_3$ | —(CO)—O—$C_2H_5$ | —(CO)—O—$C_2H_5$ |
| MC142 | $CH_3$ | $CH_3$ | $CH_3$ | H | $CH_3$ | —(CO)—O—Na | —(CO)—O—Na |
| MC143 | $R_2 + R_1$: (R_1)*—O—*(R_2) (ring) | H | $CH_3$ | H | — | | |
| MC144 | $CH_3$ | $CH_3$ | H | H | $CH_3$ | | *—(CO)—CH_2—C(O)—* |
| MC145 | $CH_3$ | $CH_3$ | H | H | (cyclopentyl ring *—*) | —CN | —(CO)—CH_3 |
| MC146 | $CH_3$ | $CH_3$ | $CH_3$ | H | H | 4-(CH_3CO-NH)-C_6H_4—* | 4-CH_3O-C_6H_4—(CO)—* |
| MC147 | *—O—* (methylenedioxy linking R_2) | $CH_3$ | $CH_3$ | H | $CH_3$ | 3-CH_3-C_6H_4—* | —(CO)(CO)O$C_2H_5$ |

TABLE MC2a-continued
| | $R_2$ | $R_3$ | Q | $R_6$ | $R_1$ | T | $R_4$ |
|---|---|---|---|---|---|---|---|
| MC148 | $R_2 + R_1$: —O—*—(R_1) *—(R_2) | $CH_3$ | t-butyl | H | H | —(CO)N($C_2H_5$)$_2$ | —CO—$CH_3$ |
| MC149 | i-propyl | i-propyl | 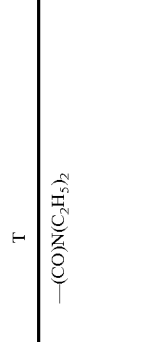 | | H | —CN | —CN |
| MC150 | $CH_3$ | $CH_3$ |  | | H | —CN | —CN |
| MC151 | —($CH_2$)$_3$—Si($CH_3$)$_3$ | | $CH_3$ | H | H | —CO—C($CH_3$)$_3$ | —CO—O—$C_2H_5$ |
| MC152 |  | | H | $CH_3$ | H | —(CO)OSi($CH_3$)$_3$ | —(CO)OSi($CH_3$)$_3$ |
| MC153 | n-$C_3H_7$ | | $CH_3$ | H | H | —CO—$CH_{33}$ |  |
| MC154 | $CH_3$ | $CH_3$ | $C_2H_5$ | H | H | —NH(CO$C_5H_{12}$ | —CN |
| MC155 | $C_2H_5$ | $C_2H_5$ | $CH_3$ | $CH_3$ | $CH_3$ | —(CO)—O—$C_2H_5$ | —(CO)—O—$C_2H_5$ |

TABLE MC2a-continued

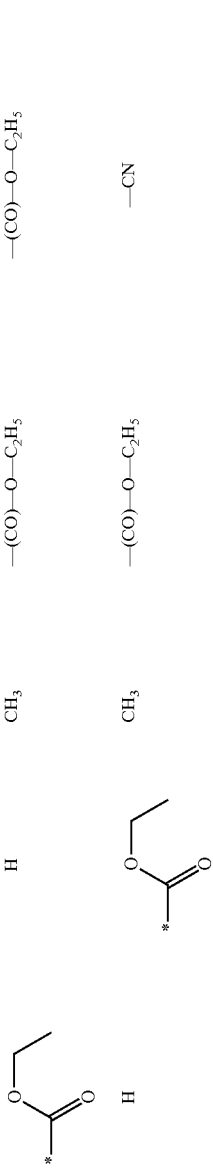

| | $R_2$ | $R_3$ | Q | $R_6$ | $R_1$ | T | $R_4$ |
|---|---|---|---|---|---|---|---|
| MC156 | $CH_3$ | $CH_3$ | 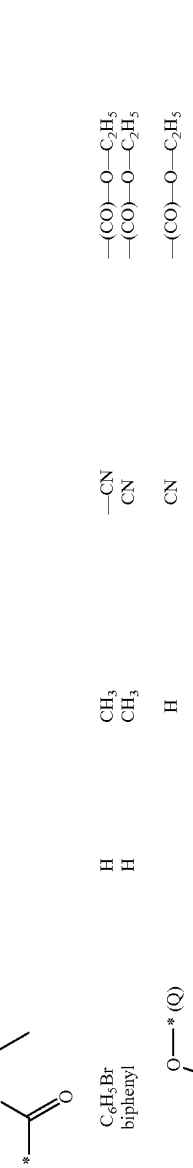 | H | $CH_3$ | —(CO)—O—$C_2H_5$ | —(CO)—O—$C_2H_5$ |
| MC157 | $CH_3$ | $CH_3$ | H | 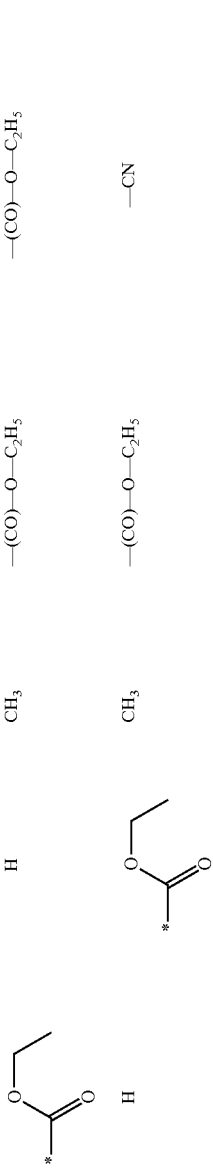 | $CH_3$ | —(CO)—O—$C_2H_5$ | —CN |
| MC158 | $CH_3$ | $CH_3$ | 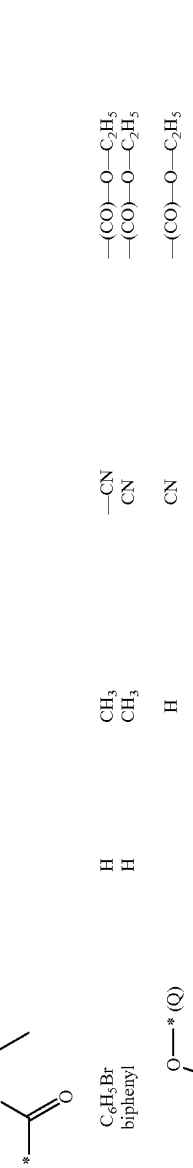 | H | phenyl | —(CO)—O—$C_2H_5$ | —(CO)—O—$C_2H_5$ |
| MC159 | $CH_3$ | $CH_3$ | $C_6H_5Br$ | H | $CH_3$ | —CN | —(CO)—O—$C_2H_5$ |
| MC160 | $CH_3$ | $CH_3$ | biphenyl | H | $CH_3$ | CN | —(CO)—O—$C_2H_5$ |
| MC161 | $CH_3$ | $CH_3$ | 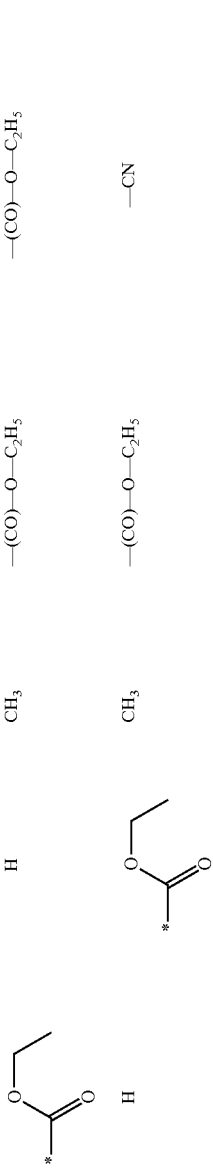 | | H | CN | —(CO)—O—$C_2H_5$ |
| MC162 | $CH_3$ | $CH_3$ | phenyl | H | $CH_3$ | CN | —(CO)—O—$C_2H_5$ |
| MC163 | 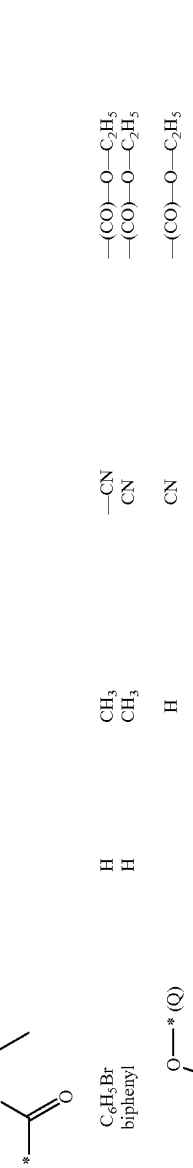 | $CH_3$ | H | H | 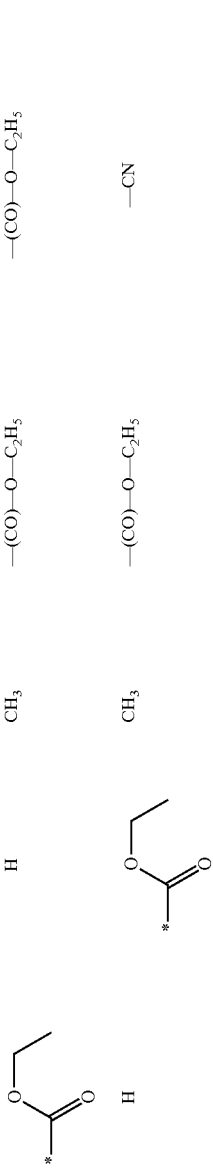 | CN | —(CO)—O—$C_2H_5$ |
| MC164 | n-butyl | n-butyl | $CH_3$ | H | H | —(CO)—O—$C_2H_5$ | —$SO_2$—$C_6H_5$ |
| MC165 | $CH_3$ | $CH_3$ | H | H | phenyl | —(CO)—$CH_3$ | 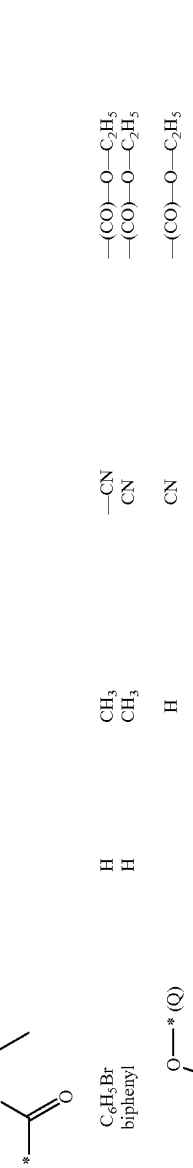 |

TABLE MC2a-continued

![structure: R2-N(R3)-C(R1)=C(R6)-C(Q)=C(R4)(T)]

| | $R_2$ | $R_3$ | Q | $R_6$ | $R_1$ | T | $R_4$ |
|---|---|---|---|---|---|---|---|
| MC166 | $CH_3$ | $CH_3$ | H | H | * —O—CH₂—CH₃ (ethoxymethyl) | —(CO)—CH₃ | —CN |
| MC167 | $CH_3$ | $CH_3$ | 2-thienyl* | H | H | —(CO)—O—CH₃ | —(CO)—O—CH₃ |
| MC168 | $CH_3$ | $CH_3$ | H | H | phenyl | —CN | —(CO)OC(CH₃)₃ |
| MC169 | n-butyl | n-butyl | H | H | 3,4-dimethoxyphenyl* | —CN | —(CO)OC(CH₃)₃ |
| MC170 | $C_2H_5$ | $C_2H_5$ | H | H | 3-(CF₃)phenyl* | —CN | —(CO)—O—CH₂CH(CH₃)₂ |
| MC171 | $CH_3$ | $CH_3$ | 4-F-phenyl* | H | 3-methylphenyl* (CH₃) | —CN | —(CO)—O—CH(CH₃)₂ |

TABLE MC2a-continued (Structure: $R_2$-N($R_3$)-C($R_1$)=C($R_6$)-C($Q$)=C($R_4$)(T))

| | $R_2$ | $R_3$ | Q | $R_6$ | $R_1$ | T | $R_4$ |
|---|---|---|---|---|---|---|---|
| MC172 | -CH(CH$_3$)-CH$_2$-CH(CH$_3$)- (R$_2$ and R$_3$ joined) | | H | H | 3,5-dimethyl-pyrrol-1-yl (*N) | —CN | isopropyl ester (*-O-C(=O)-CH(CH$_3$)$_2$) |
| MC173 | C$_2$H$_5$ | C$_2$H$_5$ | H | H | 4-methoxyphenyl | —CN | —(CO)—O—C$_2$H$_5$ |
| MC174 | CH$_3$ | CH$_3$ | H | H | —CN | —CN | —(CO)—O—CH$_3$ |
| MC175 | —C$_2$H$_4$OH | —C$_2$H$_4$OH | H | H | * | —CN | —(CO)—O—C$_2$H$_5$ |
| MC176 | H | C$_2$H$_5$ | H | H | 4-methylphenyl | —CN | —(CO)—O—C$_2$H$_5$ |

TABLE MC2a-continued
| | $R_2$ | $R_3$ | Q | $R_6$ | $R_1$ | T | $R_4$ |
|---|---|---|---|---|---|---|---|
| MC177 | $C_2H_5$ | n-butyl | 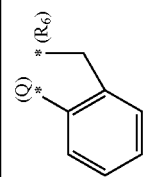 (Q) * (R$_6$) | H | H | —CN | —CN |
| MC178 | $C_2H_5$ | $C_2H_5$ | $C_2H_5$ | H | H |  (T = R$_4$) | |
| MC179 | $C_2H_5OH$ | $C_2H_5OH$ | $CH_3$ | $CH_3$ | H | —CN |  |
| MC180 | H |  | $CH_3$ | H | H | 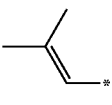 | —COCH$_3$ |

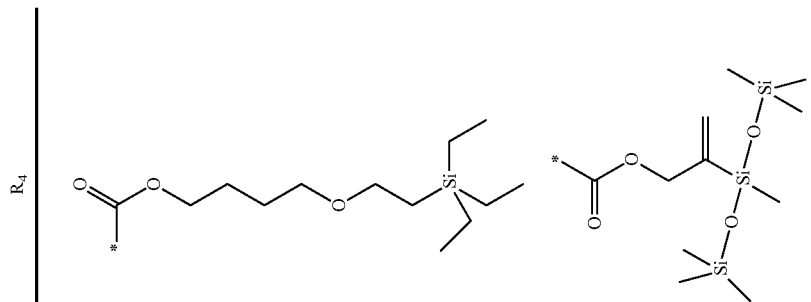

TABLE MC2a-continued

| R2 | R3 | Q | R1 | T | R4 |
|---|---|---|---|---|---|
| MC183 | | | | | |
| MC184 | | | | | |
| MC185 | | | | | |

TABLE MC2a-continued

| | R₂ | R₃ | Q | R₆ | R₁ | T | R₄ |
|---|---|---|---|---|---|---|---|
| MC186 | | | | | | | |
| MC187 | | | | | | | |
| MC188 | | | | | | | |

TABLE MC2a-continued

| | $R_2$ | $R_3$ | Q | $R_6$ | $R_1$ | T | $R_4$ |
|---|---|---|---|---|---|---|---|
| MC189 | | | | | | | |
| MC190 | | | | | | | |
| MC191 | | | | | | | |

TABLE MC2a-continued

| R2 | R3 | Q | R1 | T | R4 |
|----|----|---|----|----|----|

MC192

MC193

MC194

TABLE MC2a-continued

| | $R_2$ | $R_3$ | Q | $R_1$ | T | $R_4$ |
|---|---|---|---|---|---|---|
| MC195 | | | | | | |
| MC196 | | | | | | |
| MC197 | | | | | | |
| MC198 | | | | | | |

The compounds of formula (1) are prepared according to known processes, as disclosed for example in J. Org. Chem. USSR (Engl. Transl.) 26(8), p. 1562f (1990); J. Heterocycl. Chem. 33(3), p. 763-766 (1996); Khimiya Geterotsiklicheskikh Soedinenii 11, p. 1537-1543 (1984); Khimiya Geterotsiklicheskikh Soedinenii 3, p. 397-404 (1982); Chem. Heterocycl. Comp. (Engl. Transl.) 24(8), 914-919 (1988).

The synthesis of the compounds used in the present invention is also disclosed in WO 0234710, Eur. J. Org. Chem. 2003, 2250-2253, J. Med. Chem. 1996, 39, 1112-1124 and J. Org. Chem., Vol. 37, No. 8, 1972, 1141-1145 as follows:

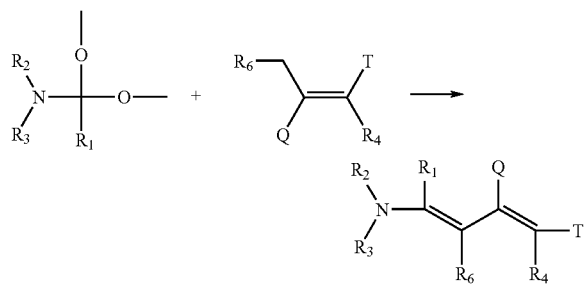

Vinylogene CH-acid compounds are reacted with acetales of amides.

In J. Heterocyclic Chem., 27, 1990, 1143-1151 aminoacrylic acid esters or aminoacrylnitriles are reacted with ethoxymethylenecyanoacetates in ethanol to the corresponding compounds used in the present invention.

In J. Prakt. Chem. 327 (1985) 4, 567-579 iminoformylation reactions are carried out on substituted crotonnitriles:

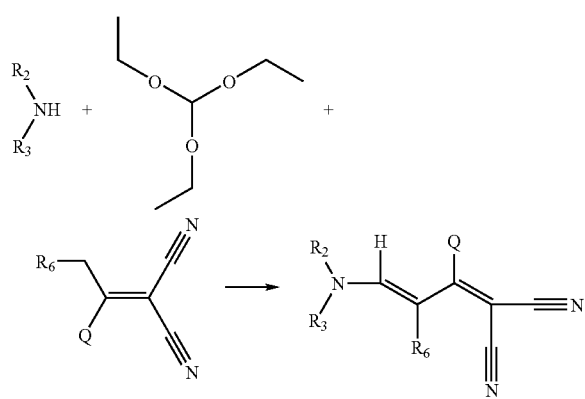

The compounds of the formula (1) according to the present invention are particularly suitable as UV filters, i.e. for protecting ultraviolet-sensitive organic materials, in particular the skin and hair of humans and animals, from the harmful effects of UV radiation. These compounds are therefore suitable as sunscreens in cosmetic, pharmaceutical and veterinary medical preparations. These compounds can be used both in dissolved form and in the micronized state.

The UV absorbers according to the present invention can be used either in the dissolved state (soluble organic filters, solubelized organic filters) or in the micronised state (nanoscalar organic filters, particulate organic filters, UV-absorber pigments).

Any known process suitable for the preparation of microparticles can be used for the preparation of the micronised UV absorbers, for example wet-milling, wet-kneading, spray-drying from a suitable solvent, by the expansion according to the RESS process (Rapid Expansion of Supercritical Solutions) by reprecipitation from suitable solvents.

The micronised UV absorbers so obtained usually have an average particle size from 0.02 to 2, preferably from 0.03 to 1.5, and more especially from 0.05 to 1.0 micrometer.

A further object of the present invention is a UV absorber dispersion, comprising
(a) a micronised UV absorber of formula (1), each of them having a particle size from 0.02 to 2 µm, and
(b) a suitable dispersing agent.

The cosmetic formulations or pharmaceutical compositions according to the present invention may additionally contain one or more than one further conventional UV filter.

The cosmetic or pharmaceutical preparations may be, for example, creams, gels, lotions, alcoholic and aqueous/alcoholic solutions, emulsions, wax/fat compositions, stick preparations, powders or ointments. In addition to the above-mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight und preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The compounds of formula (1) may also be used as an anti-wrinkle perception modifier (see Example 29). This is a further object of the present invention.

Preferably, the following combinations comprising UV absorbers are of special interest:

The cosmetic or pharmaceutical preparations may be, for example, creams, gels, lotions, alcoholic and aqueous/alcoholic solutions, emulsions, wax/fat compositions, stick preparations, powders or ointments. In addition to the above mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight und preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also contain one or one more additional compounds like fatty alcohols, esters of fatty acids, natural or synthetic triglycerides including glyceryl esters and derivatives, pearlescent waxes:hydrocarbon oils: silicones or siloxanes (organosubstituted super-fatting agents, surfactantsconsistency regulators/thickeners and rheology modifiers, polymers, biogenic active ingredients, deodorising active ingredients, anti-dandruff agents, antioxidants, hydrotopic agents, preservatives and bacteria-inhibiting agents, perfume oils, colourants, polymeric beads or hollow spheres as spf enhancers, Cosmetic or Pharmaceutical Preparations Cosmetic or pharmaceutical formulations are contained in a wide variety of cosmetic preparations. There come into consideration, for example, especially the following preparations:

skin-care preparations, e.g. skin-washing and cleansing preparations in the form of tablet-form or liquid soaps, soapless detergents or washing pastes, bath preparations, e.g. liquid. (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen per-oxide solutions, lightening shampoos, bleaching creams, bleaching powders, bleaching pastes or oils, temporary, semi-permanent or permanent hair colourants, preparations containing self-oxidising dyes, or natural hair colourants, such as henna or chamomile.

Presentation Forms

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellent gas or pump-action spray) or an aerosol, in the form of a foam, or in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

Other typical ingredients in such formulations are preservatives, bactericides and bacteriostatic agents, perfumes, dyes, pigments, thickening agents, moisturizing agents, humectants, fats, oils, waxes or other typical ingredients of cosmetic and personal care formulations such as alcohols, poly-alcohols, polymers, electrolytes, organic solvents, silicon derivatives, emollients, emulsifiers or emulsifying surfactants, surfactants, dispersing agents, antioxidants, anti-irritants and anti-inflammatory agents etc.

The cosmetic preparation according to the invention is distinguished by excellent protection of human skin against the damaging effect of sunlight.

PREPARATION EXAMPLES

Example 1

Preparation of the Compound of Formula

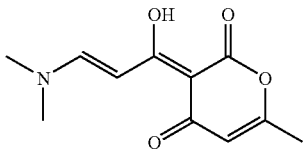

A mixture of 8.58 g of dehydroacetic acid with 7.63 g of N,N-Dimethylformamid-dimethyl-acetate in 100 ml of tert.-butylmethylether is stirred for 8 hours at room temperature. Then the product is filtered off, washed with minor amounts of tert.-butylmethylether and dried in vacuum at 40° C.

The yield is nearly quantitative. Fp: 159-161° C.

Example 2

Preparation of Compound of Formula

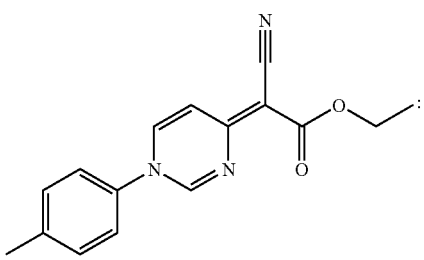

A mixture of 1 g of 1-Ethoxycarbonyl-1-cyano-2-(N-dimethylaminomethylen)amino-4-di-methylaminobutadiene (prepared according to Chem. Heterocycl. Compd. (Engl. Transl.), 24, 8, 1988, 918) with 0.43 g of p-toluidine in 10 ml of dimethylformamide is boiled for 1 hour. The solvent is evaporated, the residue is ground in ether, filtered and dried in vacuum at 40° C. yielding 0.75 g of colorless crystals. Fp: 210-216° C.

Example 3

Preparation of the Compound of Formula

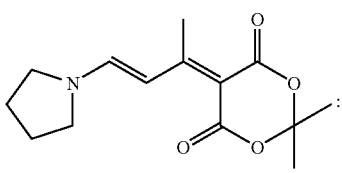

A mixture of 8.62 g pyrrolidine, 16.34 g malonic acid-cycl.-isopropylidene ester and 14.68 g acetylacetaldehyd dimethylacetal in 100 ml Toluene are stirred for 45 minutes at room temperature an kept under reflux for 67 hours.

The reaction mixture is stirred for 4 h at 3° C. and finally for 16 h at room temperature.

The raw product is filtered off and washed with diethylether and finally 4 times with 10 ml methanol.

After drying in vacuo at 60° C. 2.70 g of the product of formula (1) are obtained as bright-orange crystals.

$\lambda_{max}$=396 nm.

Example 4

Preparation of the Compound: of Formula

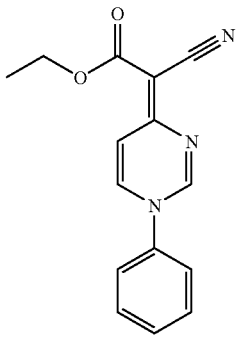

A mixture of 1.16 g of 1-Ethoxycarbonyl-1-cyano-2-(N-dimethylaminomethylen)amino-4-dimethylaminobutadiene (prepared according to Chem. Heterocycl. Compd. (Engl. Transl.), 24, 8, 1988, 918) with 0.47 g of aniline in 11 ml of acetic acid is boiled for 1 hour. After cooling to room temperature the product is filtered off, recrystallized from toluene/ethyl acetate (1:1) yielding yellow crystals which were dried in vacuum at 40° C. The yield is 25%. $\lambda_{max}$=363 nm.

Application Examples

Example 5

UV-A/UV-B Daily Care UV Protection Lotion

|  | INCI-Name | % w/w (as supplied) |
|---|---|---|
| Part A | Oleth-3 Phosphate | 0.60 |
|  | Steareth-21 | 2.50 |
|  | Steareth-2 | 1.00 |
|  | Cetyl Alcohol | 0.80 |
|  | Stearyl Alcohol | 1.50 |
|  | Tribehenin | 0.80 |
|  | Isohexadecane | 8.00 |
|  | Ethylhexyl Methoxycinnamate | 5.00 |
| Part B | Water | qs to 100 |
|  | Glycerin | 2.00 |
|  | UV-absorber as described in examples 1 to 4 | 3.00 |
|  | Disodium EDTA | 0.10 |
| Part C | Water | 20.00 |
|  | Diazolidinyl Urea (and) Iodopropynyl Butylcarbamate | 0.15 |
|  | Propylene Glycol | 4.00 |
| Part D | Sodium Acrylates Copolymer (and) Paraffinium Liquidum (and) PPG-1 Trideceth-6 | 1.50 |
|  | Cyclopentasiloxane | 4.50 |
|  | PEG-12 Dimethicone | 2.00 |

-continued

| | INCI-Name | % w/w (as supplied) |
|---|---|---|
| | Tocopheryl Acetate | 0.45 |
| | Water (and) Citric Acid | qs |
| Part E | Fragrance | qs |

Manufacturing Instruction:

Part A and part B are heated separately to 75° C. Part A is poured into part B under continuous stirring. Immediately after the emulsification, Cyclopentasiloxane and PEG-12 Dimethicone from part D are incorporated into the mixture. Afterwards the mixture is homogenized with an Ultra Turrax at 11000 rpm for 30 sec. After cooling down to 65° C. Sodium Acrylates Copolymer (and) Paraffinium Liquidum (and) PPG-1 Trideceth-6 are incorporated. Part C is added at a temperature <50° C. At a temperature ≦35° C. Tocopheryl Acetate is incorporated and subsequently the pH is adjusted with Water (and) Citric Acid. At room temperature part E is added.

Example 6

UV Day Lotion

| | INCI-Name | % w/w (as supplied) |
|---|---|---|
| Part A | Cetyl Phosphate | 1.75 |
| | C12-C15 Alkyl Benzoate | 5.00 |
| | Cetearyl Alcohol/PEG-20 Stearate | 2.00 |
| | Ethoxydiglycol Oleate | 2.00 |
| | Stearic Acid | 1.50 |
| | Ethylhexyl Methoxycinnamate | 3.00 |
| | Isononyl Isononanoate | 2.00 |
| Part B | Aqua | qs to 100 |
| | Xanthan Gum | 0.35 |
| | UV-absorber as described in examples 1 to 4 | 5.00 |
| | Disodium EDTA | 0.20 |
| | Propylene Glycol | 2.00 |
| | Diazolidinyl Urea (and) Methylparaben (and) Propylparaben (and) Propylene Glycol | 0.70 |
| | Glycerin | 1.50 |
| Part C | Cyclopentasiloxane (and) Dimethiconol | 1.00 |
| | Ethoxydiglycol | 3.00 |
| | Dimethicone | 2.00 |
| Part D | Triethanolamine | qs |

Manufacturing Instruction:

Part A is prepared by incorporating all ingredients, then stirred under moderate speed and heated to 75° C. Part B is prepared and heated to 75° C. At this temperature part B is poured into part A under progressive stirring speed. Then the mixture is homogenized (30 sec., 15000 rpm). At a temperature <55° C. the ingredients of part C are incorporated. The mixture is cooled down under moderate stirring, then the pH is checked and adjusted with triethanolamine.

Example 7

Sun Protection Emulsion

| | INCI-Name | % w/w (as supplied) |
|---|---|---|
| Part A | Cetearyl Alcohol (and) Dicetyl Phosphate10 (and) Ceteth-Phosphate | 4.00 |
| | C12-15 Alkyl Benzoate | 2.00 |
| | Dicaprylyl Ether | 3.00 |
| | Ethoxydiglycol Oleate | 2.00 |
| | Stearic Acid | 1.00 |
| | Ethylhexyl Methoxycinnamate | 3.00 |
| | Sodium Acrylates Copolymer (and) Glycine Soja (and) PPG-1 Trideceth-6 | 0.30 |
| | Squalane | 3.50 |
| Part B | Aqua | qs to 100 |
| | UV-absorber as described in examples 1 to 4 | 5.00 |
| Part C | Diazolidinyl Urea (and) Iodopropynyl Butylcarbamate | 0.15 |
| | Propylene Glycol | 2.50 |
| | Aqua | 10.00 |
| Part D | Cyclopentasiloxane, Dimethiconol | 2.00 |
| | Ethoxydiglycol | 5.00 |
| | Cyclopentasiloxane (and) Dimethicone/Vinyldimethicone Crosspolymer | 2.00 |
| Part E | Sodium Hydroxide | 0.10 |

Manufacturing Instruction:

Part A is prepared by incorporating all ingredients, then stirred under moderate speed and heated to 75° C. Part B is prepared and heated to 75° C. At this temperature, part B is poured into part A under progressive stirring speed. Below 65° C. the ingredients of part D are added separately. After cooling down under moderate stirring to 55° C. part C is added. The pH is then checked and adjusted with sodium hydroxide. The mixture is homogenized for 30 sec at 16000 rpm.

Example 8

Every Day Lotion

| | INCI-Name | % w/w (as supplied) |
|---|---|---|
| Part A | Stearyl Phosphate | 5.00 |
| | Tricontanyl PVP | 1.00 |
| | Ethoxydiglycol Oleate | 3.00 |
| | Squalane | 5.00 |
| | C12-15 Alkyl Benzoate | 5.00 |
| | Ethylhexyl Methoxycinnamate | 3.00 |
| | Glyceryl Stearate | 2.00 |
| | Cetyl Alcohol | 2.00 |
| Part B | Aqua | 20.00 |
| | UV-absorber as described in examples 1 to 4 | 3.00 |
| Part C | Aqua | qs to 100 |
| | Steareth-10 Allyl Ether/Acrylates Copolymer | 0.50 |
| | Glycerin | 2.50 |
| | Diazolidinyl Urea (and) Iodopropynyl Butylcarbamate | 0.15 |
| | Sodium Lauroyl Glutamate | 0.70 |
| Part D | Cyclopentasiloxane (and) Dimethiconol | 1.50 |
| | Triethanolamine | 1.85 |

Manufacturing Instruction:

Part A is prepared by incorporating all ingredients, then stirred under moderate speed and heated to 75° C. Part C is prepared and heated to 75° C. Part C is poured into the part A under moderate stirring. Immediately after the emulsification part B is added, then neutralized with a part of the triethanolamine. The mixture is homogenized for 30 sec. After cooling down under moderate stirring Cyclopentasiloxane (and) Dimethiconol are added. Below 35° C. the pH is checked and adjusted with triethanolamine.

Example 9

Sprayable Sunscreen Emulsion

|        | INCI-Name | % w/w (as supplied) |
|--------|-----------|---------------------|
| Part A | Ceteareth-15 (and) Glyceryl Stearate | 3.00 |
|        | Stearyl Alcohol | 1.00 |
|        | Cetyl Ricinoleate | 0.80 |
|        | Dicaprylyl Ether | 3.00 |
|        | C12-15 Alkyl Benzoate | 3.00 |
|        | Isohexadecane | 2.50 |
|        | Stearyl Dimethicone | 1.00 |
|        | Ethylhexyl Methoxycinnamate | 4.00 |
|        | Cetyl Alcohol | 0.80 |
|        | Di-C12-13 Alkyl Tartrate | 3.00 |
| Part B | Aqua | qs to 100 |
|        | Steareth-10 Allyl Ether/Acrylates Copolymer | 0.45 |
|        | PEG-7 Glyceryl Cocoate | 2.50 |
|        | Glycerin | 2.00 |
|        | Propylene Glycol | 3.00 |
| Part C | Diazolidinyl Urea (and) Iodopropynyl Butylcarbamate | 0.15 |
|        | Aqua | 20.00 |
|        | UV-absorber as described in examples 1 to 4 | 12.00 |
|        | Titanium Dioxide (and) Silica (and) Sodium Polyacrylate | 8.00 |
| Part D | Cyclopentasiloxane (and) Dimethiconol | 0.85 |
| Part E | Sodium Hydroxide (and) Water | qs to pH 6.50-7.00 |
| Part F | Fragrance | qs |

Manufacturing Instruction

Part A and part B are heated up to 80° C. Part A is blended into part B under stirring and homogenized with an UltraTurrax at 11000 rpm for 30 sec. Part C is heated to 60° C. and added slowly to the emulsion. After cooling down to 40° C. part D is incorporated at room temperature and part E is added.

Example 10

Daily Care Lotion

|        | INCI-Name | % w/w (as supplied) |
|--------|-----------|---------------------|
| Part A | Polyglyceryl Methyl Glucose Distearate | 2.50 |
|        | Cetearyl Alcohol | 2.00 |
|        | Octyl Stearate | 3.00 |
|        | Caprylic/Capric Triglyceride | 4.00 |
|        | Isohexadecane | 4.00 |
|        | Ethylhexyl Methoxycinnamate | 2.70 |
| Part B | Aqua | 64.80 |
|        | Glycerin | 5.00 |
|        | Phenoxyethanol (and) Methylparaben (and) Butylparaben (and) Ethylparaben (and) Propylparaben | 0.50 |
|        | UV-absorber as described in examples 1 to 4 | 8.00 |
| Part C | Cyclomethicone (and) Dimethicone | 3.00 |
| Part D | Steareth-10 Allyl Ether/Acrylates Copolymer | 0.50 |

Manufacturing Instruction

Part A and B are heated to 75° C. Part A is added into part B under continuous stirring and homogenized with 11000 rpm for 1 minute. After cooling down to 50° C. part C is added under continuous stirring. After cooling further down to 30° C. part D is added. Afterwards the pH is adjusted between 6.00-6.50.

Example 11

Daily Care with UV Protection

|        | INCI-Name | % w/w (as supplied) |
|--------|-----------|---------------------|
| Part A | Glyceryl Stearate SE | 3.00 |
|        | Glyceryl Stearate and PEG-100 Stearate | 3.50 |
|        | Cetyl Alcohol | 1.50 |
|        | Myristyl Myristate | 2.00 |
|        | Isopropyl Palmitate | 2.50 |
|        | Paraffinum Perliquidum | 5.00 |
|        | Octyl Dimethyl PABA | 3.00 |
| Part B | Aqua | qs to 100 |
|        | Propylene Glycol | 7.50 |
|        | Phenoxyethanol (and) Methylparaben (and) Butylparaben (and) Ethylparaben (and) Propylparaben | 1.00 |
| Part C | Aqua | 30.00 |
|        | UV-absorber as described in examples 1 to 4 | 10.00 |
| Part D | Sodium Acrylates Copolymer (and) Paraffinium Liquidum (and) PPG-1 Trideceth-6 | 2.00 |
| Part E | Citric Acid | 0.30 |

Manufacturing Instruction:

Part A and B are heated separately to 75° C. After adding part B into part A the mixture is homogenized with Ultra Turrax for one minute at 11000 rpm. After cooling down to 50° C. part C is added. Afterwards the mixture is homogenized for one minute at 16000 rpm. At a temperature <40° C. part D is added. At room temperature the pH-value is adjusted with part E between 6.00 and 6.50.

Example 12

O/W Every Day UV Protection Lotion

|        | INCI-Name | % w/w (as supplied) |
|--------|-----------|---------------------|
| Part A | Glyceryl Stearate (and) PEG-100 Stearate | 5.00 |
|        | Stearyl Alcohol | 1.00 |
|        | Tripalmitin | 0.70 |
|        | Dimethicone | 2.00 |
|        | C12-15 Alkyl Benzoate | 5.00 |
|        | Isopropyl Palmitate | 5.00 |
|        | Ethylhexyl Methoxycinnamate | 3.00 |

-continued

| INCI-Name | | % w/w (as supplied) |
|---|---|---|
| Part B | Water | qs to 100 |
| | Polysorbate 60 | 0.50 |
| | Glycerin | 3.00 |
| Part C | Water | 10.00 |
| | UV-absorber dispersion as described in examples 1 to 4 | 8.00 |
| Part D | Phenoxyethanol (and) Methylparaben (and) Ethylparaben (and) Butylparaben (and) Propylparaben (and) Isobutylparaben | 0.70 |
| | Steareth-10 Allyl Ether/Acrylates Copolymer | 1.50 |
| Part E | Water (and) Sodium Hydroxide | qs |
| Part F | Fragrance | qs |

Manufacturing Instruction:

Part A and B are heated separately up to 75° C., part C is heated to 60° C. Afterwards part B is poured into part A under stirring. The mixture is homogenized with an Ultra Turrax for 30 sec. at 11000 rpm and part C is incorporated. After cooling down to 40° C. part D is added. At room temperature the pH-value is adjusted with Sodium Hydroxide between 6.30 and 6.70 and part F is added.

Example 13

O/W Every Day UV Protection

| INCI-Name | | % w/w (as supplied) |
|---|---|---|
| Part A | Glyceryl Stearate (and) PEG-100 Stearate | 5.00 |
| | Stearyl Alcohol | 1.00 |
| | Tripalmitin | 0.70 |
| | Dimethicone | 2.00 |
| | C12-15 Alkyl Benzoate | 5.00 |
| | Isopropyl Palmitate | 5.00 |
| | Ethylhexyl Methoxycinnamate | 3.00 |
| Part B | Water | qs to 100 |
| | Polysorbate 60 | 0.50 |
| | Glycerin | 3.00 |
| Part C | Water | 10.00 |
| | UV-absorber dispersion as described in examples 1 to 4 | 8.00 |
| Part D | Phenoxyethanol (and) Methylparaben (and) Ethylparaben (and) Butylparaben (and) Propylparaben (and) Isobutylparaben | 0.70 |
| | Steareth-10 Allyl Ether/Acrylates Copolymer | 1.50 |
| Part E | Water (and) Sodium Hydroxide | qs |
| Part F | Fragrance | qs |

Manufacturing Instruction:

Part A and B are heated separately up to 75° C., part C is heated to 60° C. Afterwards part B is poured into part A under stirring. The mixture is homogenized with an Ultra Turrax for 30 sec. at 11000 rpm and part C is incorporated. After cooling down to 40° C. part D is added. At room temperature the pH-value is adjusted with Sodium Hydroxide between 6.30 and 6.70 and part F is added.

Example 14

Sunscreen Cream

| INCI-Name | | % w/w (as supplied) |
|---|---|---|
| Part A | Cetearyl Alcohol (and) Dicetyl Phosphate (and) Ceteth-10 Phosphate | 4.50 |
| | C12-15 Alkyl Benzoate | 6.00 |
| | Caprylic/Capric Triglyceride | 7.00 |
| | Pentaerythritol Tetraisostearate | 2.00 |
| | Ethylhexyl Methoxycinnamate | 3.00 |
| | Isoamyl p-Methoxycinnamate | 2.00 |
| Part B | Aqua | qs to 100 |
| | Glycerin | 2.00 |
| | Propylene Glycol | 1.50 |
| | Magnesium Aluminium Silicate | 1.20 |
| Part C | Steareth-10 Allyl Ether/Acrylates Copolymer | 0.50 |
| | UV-absorber dispersion as described in examples 1 to 4 | 12.00 |
| Part D | Phenyl Trimethicone | 1.50 |
| | Phenoxyethanol (and) Methylparaben (and) Butylparaben (and) Ethylparaben (and) Propylparaben | 0.70 |
| Part E | Sodium Hydroxide | 0.90 |

Manufacturing Instruction:

Part A and part B are heated separately to 75° C. Part B is added into part A under continuous stirring and afterwards homogenized with Ultra Turrax for 30 sec at 11000 rpm. After cooling down to 60° C. part C is added. At 40° C. part C is added and homogenized for 15 sec at 11000 rpm. At room temperature the pH-value is adjusted with part E.

Example 15

UVA/UVB Daily Care Lotion, Type O/W

| INCI-Name | | % w/w (as supplied) |
|---|---|---|
| Part A | Glyceryl Stearate (and) PEG-100 Stearate | 5.00 |
| | Stearyl Alcohol | 1.00 |
| | Tripalmitin | 0.70 |
| | Mineral Oil | 15.00 |
| Part B | Water | qs to 100 |
| | Polysorbate 60 | 0.50 |
| | Glycerin | 3.00 |
| Part C | Water | 10.00 |
| | UV-absorber dispersion as described in examples 1 to 4 | 8.00 |
| Part D | Steareth-10 Allyl Ether/Acrylates Copolymer | 1.50 |
| | Phenoxyethanol (and) Methylparaben (and) Ethylparaben (and) Butylparaben (and) Propylparaben (and) Isobutylparaben | 0.70 |
| Part E | Water (and) Sodium Hydroxide | qs |
| Part F | Fragrance | qs |

Manufacturing Instruction:

Part A and B are heated separately to 75° C.; part C to 60° C. Part B is poured into part A under stirring. After one-minute of homogenization at 11000 rpm part C is added to the mixture of A/B. After cooling down to 40° C. part D is incorporated. At room temperature the pH value is adjusted with part E between 6.3 and 7.0. Finally part F is added.

Example 16

UVA/UVB Daily Care Lotion, Type O/W

| | INCI-Name | % w/w (as supplied) |
|---|---|---|
| Part A | Oleth-3 Phosphate | 0.60 |
| | Steareth-21 | 2.50 |
| | Steareth-2 | 1.00 |
| | Cetyl Alcohol | 0.80 |
| | Stearyl Alcohol | 1.50 |
| | Tribehenin | 0.80 |
| | Isohexadecane | 8.00 |
| Part B | Water | qs to 100 |
| | Glycerin | 2.00 |
| | Disodium EDTA | 0.10 |
| Part C | Cyclopentasiloxane | 4.50 |
| | PEG-12 Dimethicone | 2.00 |
| Part D | Sodium Acrylates Copolymer (and) Mineral Oil (and) PPG-1 Trideceth-6 | 1.50 |
| Part E | UV-absorber dispersion as described in examples 1 to 4 | 10.00 |
| Part F | Tocopheryl Acetate | 0.45 |
| | DMDM Hydantoin (and) Iodopropynyl Butylcarbamate (and) Aqua (and) Butylene Glycol | 0.85 |
| Part G | Water (and) Citric Acid | qs |
| | Fragrance | qs |

Manufacturing Instruction:

Part A and part B are heated separately to 75° C. Part A is poured into part B under stirring. Immediately after the emulsification, part C is added to the mixture and homogenized with an Ultra Turrax at 11000 rpm for 30 sec. After cooling down to 65° C. Sodium Acrylates Copolymer (and) Mineral Oil (and) PPG-1 Trideceth-6 At 50° C. is added slowly to the UV absorber dispersion. At about 35-30° C. part F is incorporated. The pH is adjusted with part G between 5.5 and 6.5.

Example 17

UV-A/UV-B Every Day Protection Lotion O/W

| | INCI-Name | % w/w (as supplied) |
|---|---|---|
| Part A | Glyceryl Dilaurate | 2.00 |
| | Ethylhexyl Palmitate | 6.00 |
| | Cetyl Alcohol | 1.00 |
| | Glyceryl Stearate | 2.00 |
| | Laureth-23 | 1.00 |
| | Isopropyl Palmitate | 2.00 |
| | Tribehenin | 0.80 |
| | Beeswax | 1.50 |
| | Lanolin Oil | 1.00 |
| Part B | Water | qs to 100 |
| | Propylene Glycol | 4.00 |
| | Water (and) Titanium Dioxide (and) Alumina (and) Sodium Meta-phosphate (and) Phenoxyethanol (and) Sodium Methylparaben | 4.00 |
| Part C | Steareth-10 Allyl Ether/Acrylates Copolymer | 1.00 |
| Part D | Phenoxyethanol (and) Methylparaben (and) Ethylparaben (and) Butylparaben (and) Propylparaben (and) Isobutylparaben | 1.00 |

-continued

| | INCI-Name | % w/w (as supplied) |
|---|---|---|
| | UV-absorber dispersion as described in examples 1 to 4 | 8.00 |
| Part E | Water (and) Sodium Hydroxide | qs |

Manufacturing Instruction:

Part A and part B are heated separately up to 80° C. Part A is poured into part B while stirring and homogenized with an Ultra Turrax by 11000 rpm for 30 sec. After cooling down to 60° C. part C is incorporated. At 40° C. part D is added slowly under continuous stirring. The pH is adjusted with part E between 6.50-7.00.

Example 18

Sprayable Sunscreen Lotion

| | INCI-Name | % w/w (as supplied) |
|---|---|---|
| Part A | Potassium Cetyl Phosphate | 0.20 |
| | Isohexadecane | 7.00 |
| | VP/Eicosene Copolymer | 1.50 |
| | Di-C12-13 Alkyl Tartrate | 6.00 |
| | Ethylhexyl Triazone | 2.50 |
| | C12-15 Alkyl Benzoate | 4.50 |
| Part B | Water | qs to 100 |
| | Sorbeth-30 | 2.00 |
| | Sorbitan Stearate (and) Sucrose Cocoate | 4.00 |
| | Titanium Dioxide (and) Alumina (and) Silica (and) Sodium Polyacrylate | 2.50 |
| Part C | Water | 30.00 |
| | UV-absorber dispersion as described in examples 1 to 4 | 12.00 |
| Part D | Phenoxyethanol (and) Methylparaben (and) Ethylparaben (and) Butylparaben (and) Propylparaben (and) Isobutylparaben | 0.70 |
| Part E | Water (and) Citric Acid | qs |

Manufacturing Instruction:

Part A and part B are heated separately up to 80° C., part C is heated to 50° C. Part B is poured into part A and homogenized with an Ultra Turrax for 1 minute at 11000 rpm. After cooling down to 50° C. part C is added under continuous stirring. At 40° C. part D is incorporated and homogenized again for 10 sec. at 11000 rpm. The pH is adjusted with part E.

Example 19

O/W Every Day UV Protection Lotion

| | INCI-Name | % w/w (as supplied) |
|---|---|---|
| Part A | Glyceryl Stearate (and) PEG-100 Stearate | 5.00 |
| | Stearyl Alcohol | 1.00 |
| | Tripalmitin | 0.70 |
| | Dimethicone | 2.00 |
| | Caprylic/Capric Triglyceride | 5.00 |

-continued

| | INCI-Name | % w/w (as supplied) |
|---|---|---|
| | Isopropyl Palmitate | 5.00 |
| | Ethylhexyl Methoxycinnamate | 3.00 |
| Part B | Water | qs to 100 |
| | Polysorbate 60 | 0.50 |
| | Glycerin | 3.00 |
| Part C | Water | 10.00 |
| | UV-absorber dispersion as described in examples 1 to 4 | 8.00 |
| Part D | Phenoxyethanol (and) Methylparaben (and) Ethylparaben (and) Butylparaben (and) Propylparaben (and) Isobutylparaben | 0.70 |
| | Steareth-10 Allyl Ether/Acrylates Copolymer | 1.50 |
| Part E | Water (and) Sodium Hydroxide | qs |
| Part F | Fragrance | qs |

Manufacturing Instruction:

Part A and part B are heated separately up to 75° C., part C is heated to 60° C. Afterwards part B is poured into part A under stirring. The mixture is homogenized with an Ultra Turrax for 30 sec. at 11000 rpm and part C is incorporated. After cooling down to 40° C. part D is added. At room temperature the pH-value is adjusted with Sodium Hydroxide between 6.30 and 6.70 and part F is added.

Example 20

Water Resistant Sunscreen Emulsion

| | INCI-Name | % w/w (as supplied) |
|---|---|---|
| Part A | Polyglyceryl-10 Pentastearate (and) Behenyl Alcohol (and) Sodium Stearoyl Lactylate | 2.50 |
| | VP/Eicosene Copolymer | 1.50 |
| | Stearyl Alcohol | 1.50 |
| | Squalane | 4.00 |
| | C12-15 Alkyl Benzoate | 7.50 |
| | Octocrylene | 1.50 |
| | 4-Methylbenzylidene Camphor | 3.00 |
| | Ethylhexyl Methoxycinnamate | 2.00 |
| Part B | Water | qs to 100 |
| | Glycerin | 1.80 |
| | Steareth-10 Allyl Ether/Acrylates Copolymer | 0.80 |
| Part C | UV-absorber dispersion as described in examples 1 to 4 | 9.00 |
| Part D | VP/Hexadecene Copolymer | 2.70 |
| | Cyclomethicone | 1.50 |
| | Phenoxyethanol (and) Methylparaben (and) Ethylparaben (and) Butylparaben (and) Propylparaben (and) Isobutylparaben | 0.70 |
| Part E | Aqua (and) Tocopheryl Acetate (and) Caprylic/Capric Triglyceride (and) Polysorbate 80 (and) Lecithin | 3.50 |
| Part F | Fragrance | qs |
| | Water (and) Sodium Hydroxide | qs |

Manufacturing Instruction:

Part A and part B are heated separately to 80° C. Part A is poured into part B under continuous stirring. Afterwards the mixture is homogenized with an Ultra Turrax at 11000 rpm for 1 min. After cooling down to 60° C. part C is incorporated. At 40° C. part D is added and the mixture homogenized for a short time again. At 35° C. part E is added and at room temperature Fragrance is added. Finally the pH is adjusted with Sodium Hydroxide.

Example 21

UVA/UVB Sun Protection Lotion, O/W Type

| | INCI-Name | % w/w (as supplied) |
|---|---|---|
| Part A | Potassium Cetyl Phosphate | 2.00 |
| | Tricontanyl PVP | 1.00 |
| | Caprylic/Capric Triglyceride | 5.00 |
| | C12-15 Alkyl Benzoate | 5.00 |
| | Cetearyl Isononanoate | 5.00 |
| | Glyceryl Stearate | 3.00 |
| | Cetyl Alcohol | 1.00 |
| | Dimethicone | 0.10 |
| | Ethylhexyl Methoxycinnamate | 5.00 |
| Part B | Water | qs to 100 |
| | Glycerin | 3.00 |
| Part C | Steareth-10 Allyl Ether/Acrylates Copolymer | 0.50 |
| Part D | UV-absorber dispersion as described in examples 1 to 4 | 8.00 |
| Part E | Phenoxyethanol (and) Methylparaben (and) Ethylparaben (and) Butylparaben (and) Propylparaben (and) Isobutylparaben | 1.00 |
| Part F | Water (and) Sodium Hydroxide | qs to pH 7.00 |
| Part G | Fragrance | qs |

Manufacturing Instruction:

Part A and part B are heated separately up to 80° C. Part B is poured into part A under moderate stirring. The mixture is homogenized with an Ultra Turrax at 11000 rpm for 1 minute. After cooling down to 70° C. part C is added under stirring. After cooling further down to 50° C. part D is incorporated very slowly. At 40° C. part E is added. At room temperature the pH is adjusted with part F to 7.00 and part G is added.

Example 22

UVA/UVB Sun Protection Lotion, O/W Type

| | INCI-Name | % w/w (as supplied) |
|---|---|---|
| Part A | Potassium Cetyl Phosphate | 2.00 |
| | Tricontanyl PVP | 1.00 |
| | Caprylic/Capric Triglyceride | 5.00 |
| | C12-15 Alkyl Benzoate | 5.00 |
| | Cetearyl Isononanoate | 5.00 |
| | Glyceryl Stearate | 3.00 |
| | Cetyl Alcohol | 1.00 |
| | Dimethicone | 0.10 |
| | Ethylhexyl Methoxycinnamate | 5.00 |
| Part B | Water | qs to 100 |
| | Glycerin | 3.00 |
| Part C | Steareth-10 Allyl Ether/Acrylates Copolymer | 0.50 |
| Part D | UV-absorber dispersion as described in examples 1 to 4 | 20.00 |
| Part E | Phenoxyethanol (and) Methylparaben (and) Ethylparaben (and) Butylparaben (and) Propylparaben (and) Isobutylparaben | 1.00 |
| Part F | Water (and) Sodium Hydroxide | qs to pH 7.00 |
| Part G | Fragrance | qs |

Manufacturing Instruction:

Part A and part B are heated separately up to 80° C. Part B is poured into part A under moderate stirring. The mixture is homogenized with an Ultra Turrax at 11000 rpm for 1 minute. After cooling down to 70° C. add part C is added under stirring. After cooling further down to 50° C. part D is incorporated very slowly. At 40° C. part E is added. At room temperature the pH is adjusted with part F to 7.00 and part G is added.

Example 23

Sunscreen Lotion

| | INCI-Name | % w/w (as supplied) |
|---|---|---|
| Part A | Cetearyl Alcohol (and) Dicetyl Phosphate (and) Ceteth-10 Phosphate | 4.00 |
| | C12-15 Alkyl Benzoate | 2.00 |
| | Dicaprylyl Ether | 3.00 |
| | Ethoxydiglycol Oleate | 2.00 |
| | Stearic Acid | 1.00 |
| | Ethylhexyl Methoxycinnamate | 3.00 |
| | Sodium Acrylates Copolymer (and) Glycine Soja (and) PPG-1 Trideceth-6 | 0.30 |
| | Squalane | 3.50 |
| | VP/Eicosene Copolymer | 2.00 |
| Part B | Water | qs to 100 |
| | UV-absorber dispersion as described in examples 1 to 4 | 5.00 |
| Part C | Diazolidinyl Urea (and) Iodopropynyl Butylcarbamate | 0.15 |
| | Propylene Glycol | 2.50 |
| | Water | 10.00 |
| Part D | Cyclopentasiloxane (and) Dimethiconol | 2.00 |
| | Ethoxydiglycol | 5.00 |
| | Cyclopentasiloxane (and) Dimethicone/Vinyl Dimethicone Crosspolymer | 2.00 |
| Part E | Aqua (and) Sodium Hydroxide | qs |
| Part F | Fragrance | qs |

Manufacturing Instruction

Part A and part B are heated separately up to 75° C. Part B is poured into part A under progressive stirring speed. At a temperature <65° C. the ingredients of part D are added separately. After cooling down to 55° C. under moderate stirring part C is added. At a temperature <35° C. the pH is checked and adjusted with Sodium Hydroxide and homogenized with an Ultra Turrax for 30 sec. at 11000 rpm. Part F is added at room temperature.

Example 24

W/O Sunscreen Lotion

| | INCI-Name | % w/w (as supplied) |
|---|---|---|
| Part A | PEG-7 Hydrogenated Castor Oil | 3.00 |
| | Polyglyceryl-3 Diisostearate | 4.00 |
| | Microcrystalline Wax | 1.00 |
| | Magnesium Stearate | 1.50 |
| | Propylparaben | 0.10 |
| | Mineral Oil | 15.00 |
| | Octyldodecanol | 8.00 |

-continued

| | INCI-Name | % w/w (as supplied) |
|---|---|---|
| | Ethylhexyl Triazone | 1.00 |
| | Ethylhexyl Methoxycinnamate | 2.00 |
| Part B | Water | qs to 100 |
| | Water (and) Citric Acid | 0.05 |
| | Methylparaben | 0.15 |
| | Magnesium Sulfate | 0.50 |
| Part C | UV-absorber dispersion as described in example 1 or 2 | 9.00 |
| | Fragrance | qs |

Manufacturing Instruction:

Part A is heated to 80° C. whilst stirring. Part B is added into part A and homogenized with an Ultra Turrax at 11000 rpm for one minute. After cooling down to 30° C. part C is incorporated.

Example 25

Skin Protection Sunscreen Lotion W/O

| | INCI-Name | % w/w (as supplied) |
|---|---|---|
| Part A | Polyglyceryl-2 Dipolyhydroxystearate | 3.00 |
| | Glyceryl Oleate | 3.00 |
| | Cetearyl Isononanoate | 7.00 |
| | Hexyl Laurate | 6.00 |
| | Dicaprylyl Ether | 6.00 |
| | Propylparaben | 0.10 |
| | Hexyldecanol | 3.00 |
| | Magnesium Stearate | 1.00 |
| | Beeswax | 1.00 |
| | Ethylhexyl Methoxycinnamate | 4.00 |
| Part B | Water | qs to 100 |
| | Methylparaben | 0.15 |
| | Magnesium Sulfate | 1.00 |
| Part C | UV-absorber dispersion as described in examples 1 to 4 | 6.00 |

Manufacturing Instruction:

Part A is heated separately to 80° C. under gentle stirring. Part B is added to part A and homogenized for one minute at 11000 rpm. After cooling down to 30° C. part C is added under continuous stirring.

Example 26

O/W Emulsion

| | INCI-Name | % w/w (as supplied) |
|---|---|---|
| Part A | UV absorber of formula (MC 14) | 3 g |
| | sesame oil | 10 g |
| | glyceryl stearate | 4 g |
| | stearic acid | 1 g |
| | cetyl alcohol | 0.5 g |
| | polysorbate 20 | 0.2 g |
| Part B | propylene glycol | 4 g |
| | propylparaben | 0.05 g |
| | methylparaben | 0.15 g |

-continued

| INCI-Name | % w/w (as supplied) |
|---|---|
| triethanolamine | 0.1 g |
| carbomer 934 | 0.1 g |
| water | ad 100 ml |

Preparation of the Emulsion

Phase (A):

Firstly, the UV absorber is dissolved in sesame oil. The other components of (A) are added thereto and combined.

Phase (B):

Propylparaben and methylparaben are dissolved in propylene glycol. 60 ml of water are then added, heating to 70° C. Is carried out and then carbomer 934 is emulsified therein.

Emulsion:

(A) is slowly added to (B) with vigorous application of mechanical energy. The volume is adjusted to 100 ml by the addition of water.

Example 27

Daily Care Cream, Type O/W

| | INCI name | % w/w (as used) |
|---|---|---|
| Part A | Glyceryl stearate (and) cetearyl alcohol (and) cetyl palmitate (and) cocoglycerides | 4.0 |
| | Ceteareth-12 | 4.0 |
| | Cetearyl alcohol | 2.0 |
| | Dicaprylyl ether | 4.5 |
| | Ethylhexyl stearate | 4.0 |
| | Hexyl laurate | 3.5 |
| | Ethylhexyl triazone | 1.0 |
| | Benzylidene malonate polysiloxane | 2.0 |
| | HDI/trimethylol hexyl-lactone crosspolymer (and) silica | 5.0 |
| | Stearyl dimethicone | 1.0 |
| | Dimethicone | 2.0 |
| | Cetyl alcohol | 0.8 |
| | compound of formula (MC 14) | 2.0 |
| Part B | Water | q.s. to 100 |
| | Water (and) scleroglucan (and) phenoxyethanol | 2.0 |
| | Glycerol | 2.0 |
| Part C | Steareth-10 allyl ether/acrylate copolymer | 0.45 |
| | Phenoxyethanol (and) methylparaben (and) ethylparaben (and) butylparaben (and) propylparaben (and) isobutylparaben | 0.7 |
| Part D | Aqua (and) tocopheryl acetate (and) caprylic/capric triglyceride (and) polysorbate 80 (and) lecithin | 4.0 |
| Part E | Water (and) sodium hydroxide | q.s. |
| | Fragrance | q.s. |

Preparation Procedure:

Part A and part B are heated separately to 80° C. Part A is poured into part B, whilst stirring continuously. Afterwards the mixture is homogenized with an Ultra Turrax at 11000 rpm for 20 sec. The mixture is cooled to 60° C. and part C is added. At a temperature below 30° C., part D is added and the pH value is adjusted with sodium hydroxide to between 6.5 and 7.0. Finally, fragrance is added.

Example 28

Sun-Protection Cream. Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | compound of formula (MC 14) | 2.0 |
| | Ethylhexyl methoxycinnamate | 5.0 |
| | Cetyl alcohol | 0.7 |
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure

Part A and part B are heated separately to 75° C. Part A is poured into part B whilst stirring. The mixture is homogenised with an Ultra Turrax at 11000 rpm for 15 sec. The mixture is cooled to 60° C. and part C and part D are incorporated. The mixture is homogenised again for a short time (5 sec./11000 rpm) and further cooled, with moderate stirring. At room temperature, the pH is adjusted with sodium hydroxide solution to between 5.5 and 6.0. Finally, fragrance is added.

Example 29

Daily Care UV-Protection Lotion

| | INCI name | % w/w (as used) |
|---|---|---|
| Part A | Oleth-3 phosphate | 0.6 |
| | Steareth-21 | 2.5 |
| | Steareth-2 | 1.0 |
| | Cetyl alcohol | 0.8 |
| | Stearyl alcohol | 1.5 |
| | Tribehenin | 0.8 |
| | Isohexadecane | 8.0 |
| | compound of formula (MC 14) | 5.0 |
| Part B | Water | q.s. to 100 |
| | Glycerol | 2.0 |
| | Methylene bis-benzotriazolyl tetramethylbutylphenol (and) aqua (and) decyl glucoside (and) propylene glycol (and) xanthan gum | 3.0 |
| | Disodium EDTA | 0.1 |
| Part C | Water | 20.0 |
| | Diazolidinyl urea (and) iodopropynyl butylcarbamate | 0.15 |
| | Propylene glycol | 4.0 |
| Part D | Sodium acrylate copolymer (and) liquid paraffin (and) PPG-1 trideceth-6 | 1.5 |

-continued

| | INCI name | % w/w (as used) |
|---|---|---|
| | Cyclopentasiloxane | 4.5 |
| | PEG-12 dimethicone | 2.0 |
| | Tocopheryl acetate | 0.45 |
| | Water (and) citric acid | q.s. |
| Part E | Fragrance | q.s. |

Preparation Procedure

Heat part A and part B separately to 75° C. Pour part A into part B, whilst stirring continuously. Immediately after emulsification, incorporate in the mixture SF 1202 and SF 1288 from part D. Afterwards homogenise with an Ultra Turrax at 11000 rpm for 30 sec. Allow to cool to 65° C. and incorporate SALCARE® SC91. At a temperature below 50° C., add part C. At 35° C. or below, incorporate vitamin E acetate and subsequently adjust the pH with citric acid. At room temperature, add part E.

Example 30

Sun-Protection Cream, Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | compound of formula (MC 14) | 2.0 |
| | Ethylhexyl methoxycinnamate | 5.0 |
| | Cetyl alcohol | 0.7 |
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure:

Part A and part B are heated separately to 75° C. Part A is poured into part B whilst stirring. The mixture is homogenised with an Ultra Turrax at 11000 rpm for 15 sec. The mixture is cooled to 60° C., and part C and part D are incorporated. The mixture is homogenised again for a short time (5 sec./11000 rpm). After further cooling, with moderate stirring, the pH is adjusted with sodium hydroxide at room temperature. A solution between pH 5.50 and 6.00 is obtained. Finally, fragrance is added.

Example 31

Sun-Protection Cream. Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | Mixture of the compound of formula (MC 14) (50%) and Uvinul A Plus CAS Reg. No. 302776-68-7 (50%) | 2.0 |
| | Ethylhexyl methoxycinnamate | 5.0 |
| | Cetyl alcohol | 0.7 |
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure:

Part A and part B are heated separately to 75° C. Part A is poured into part B whilst stirring. The mixture is homogenised with an Ultra Turrax at 11000 rpm for 15 sec. After cooling 60° C., part C and part D are incorporated. The mixture is homogenised again for a short time (5 sec./11000 rpm). After further cooling, with moderate stirring, the pH is adjusted at room temperature with sodium hydroxide solution to between 5.50 and 6.00. Finally, fragrance is added.

Example 32

Sun-Protection Cream, Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | Mixture of compound of formula (MC 14) (50%) and benzylidene camphor, CAS Reg. No. 36861-47-9 (50%) | 2.0 |
| | Ethylhexyl methoxycinnamate | 5.0 |
| | Cetyl alcohol | 0.7 |
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure

Part A and part B are heated separately to 75° C. Part A is poured into part B whilst stirring. The mixture is homogenised with an Ultra Turrax at 11000 rpm for 15 sec. After cooling to 60° C., part C and part D are incorporated. The mixture is homogenised again for a short time (5 sec./11000 rpm). After further cooling, with moderate stirring, the pH is adjusted at room temperature with sodium hydroxide. A solution between pH 5.50 and 6.00 is obtained. Finally, fragrance is added.

The invention claimed is:

1. A method of protecting human hair and skin against the damaging effect of UV radiation, said method comprising applying to the hair and/or skin a cosmetic, pharmaceutical or veterinary preparation comprising compounds of formula

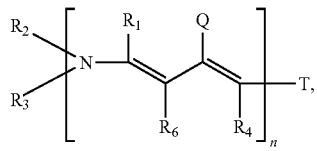

(1)

wherein

Q is hydrogen; $C_1$-$C_{22}$alkyl; —OH; —$OR_7$; —$NR_7R_8$; or —N=$R_9$;

$R_1$ is hydrogen; $C_1$-$C_{22}$alkyl; —$OR_7$; —$SR_7$; —$NR_7R_8$; $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; $C_7$-$C_{12}$aralkyl; $C_1$-$C_{12}$heteroalkyl, $C_2$-$C_{11}$heteroaralkyl; $C_6$-$C_{10}$aryl; or $C_1$-$C_9$heteroaryl;

$R_4$ is cyano; $COR_7$, $COOR_7$; $CONR_7R_8$; $SO_2(C_6$-$C_{12})$aryl; $C_2$-$C_{12}$alk-1-enyl; $C_3$-$C_{12}$cycloalk-1-enyl; $C_2$-$C_{12}$alk-1-inyl; $C_2$-$C_{12}$heteroalkyl; $C_3$-$C_5$heterocycloalkyl; $C_6$-$C_{10}$aryl; or $C_1$-$C_9$heteroaryl;

$R_5$ is —$COR_7$; —$COOR_7$; —$OR_7$; —$SR_7$; —$NHR_7$, —$NR_7R_8$; $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; $C_7$-$C_{12}$aralkyl; $C_1$-$C_{12}$alkylphenyl; $C_1$-$C_{12}$alkoxy-$C_6$-$C_{10}$aryl; $C_1$-$C_{12}$heteroalkyl; $C_2$-$C_{11}$heteroaralkyl; $C_3$-$C_{12}$cycloheteroalkyl; $C_6$-$C_{10}$aryl; $C_1$-$C_{12}$alkoxy-$C_6$-$C_{10}$aryl; or $C_1$-$C_9$heteroaryl;

$R_6$ is hydrogen; $C_1$-$C_{22}$alkyl; $C_1$-$C_{22}$alkoxy; or $COR_7$;

$R_7$ and $R_8$ independently from each other are hydrogen; $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; —$(CH_2)_t$COOH; $C_7$-$C_{12}$aralkyl; $C_1$-$C_{12}$heteroalkyl; $C_2$-$C_{11}$heteroaralkyl; $C_6$-$C_{10}$aryl; $C_1$-$C_9$heteroaryl; Si—$R_{10}R_{11}R_{12}$; Si($OR_{10}$)($OR_{11}$)($OR_{12}$); $SiR_{10}$($OR_{11}$)($OR_{12}$); $SiR_{10}R_{11}$($OR_{12}$); —$(CH_2)_u$—O—$(CH_2)_v$—$SiR_{10}R_{11}R_{12}$; or a radical X-Sil;

t, u and v, independently from each other are a number from 1 to 5;

$R_9$ is a ($C_1$-$C_6$)alkylidene radical;

$R_{10}$, $R_{11}$, $R_{12}$ independently from each other are $C_1$-$C_{22}$alkyl;

X is a linker;

Sil is a silane-, oligosiloxane- or polysiloxane radical;

$R_1$ and $R_2$, $R_1$ and Q, $R_1$ and $R_6$, $R_1$ and T, $R_2$ and $R_3$, $R_2$ and $R_4$, $R_2$ and $R_6$, $R_2$ and Q, $R_4$ and $R_6$, $R_4$ and T, $R_6$ and Q, T and Q, each independently, are linked together, so that 1, 2, 3 or 4 carbocyclic or N, O and/or S-heterocyclic rings are formed, wherein each of them, independently from each other, may be condensed with an aromatic or heteroaromatic ring, and/or more N-, O- and/or S-heterocyclic rings, and each N atom in a N-heterocyclic ring may be substituted by $C_1$-$C_{22}$alkyl;

n is a number from 1 to 4; wherein at least one of the radicals $R_1$, $R_6$ or Q is different from hydrogen;

if n=1

T is —$COR_5$; —CN; $C_6$-$C_{10}$aryl; —$NHR_5$; or —$SO_2$—($C_6$-$C_{12}$)aryl;

$R_2$ and $R_3$ independently from each other are $C_1$-$C_{22}$alkyl; hydroxy-$C_1$-$C_{22}$alkyl; $C_2$-$C_{12}$alkenyl; $C_2$-$C_{12}$alkinyl; $C_3$-$C_{12}$cycloalkyl, $C_3$-$C_{12}$cycloalkenyl; $C_7$-$C_{12}$aralkyl; $C_1$-$C_{12}$heteroalkyl; $C_3$-$C_{12}$cycloheteroalkyl; $C_6$-$C_{10}$aryl; $C_1$-$C_9$heteroaryl; or a radical of formula

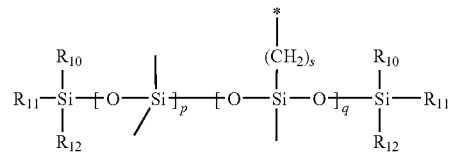

p is a number from 5 to 100
q is a number from 1 to 5;
s is a number from 0 to 4;

if n=2

$R_2$ and $R_3$ are each $C_1$-$C_5$alkylene; and simultaneously T is defined as for n=1; or T is a bivalent radical of formula —$NR_7$—V—$NR_7$—, wherein V is phenylene; or $C_1$-$C_5$alkylene;

$R_7$ is hydrogen; or $C_1$-$C_5$alkyl; and $R_2$ and $R_3$ simultaneously are defined as for n=1;

if n=3 one of $R_2$, $R_3$ or T is a trivalent radical; and if n=4 one of $R_2$, $R_3$ or T is a tetravalent radical.

2. A method according to claim 1, wherein in formula (1)

Q is —OH; —$OR_7$; —$NR_7R_8$; or —N=$R_9$;

T is —$COR_5$; —CN; or —$SO_2$—($C_6$-$C_{12}$)aryl;

$R_1$ is hydrogen; —$OR_7$, —$SR_7$; —$NR_7R_8$; $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; $C_7$-$C_{12}$aralkyl; $C_1$-$C_{12}$heteroalkyl; $C_2$-$C_{11}$heteroaralkyl; $C_6$-$C_{10}$aryl; or $C_1$-$C_9$heteroaryl;

$R_2$ and $R_3$ independently from each other are $C_1$-$C_{22}$alkyl; $C_2$-$C_{12}$alkenyl; $C_2$-$C_{12}$alkinyl; $C_3$-$C_{12}$cycloalkyl, $C_3$-$C_{12}$cycloalkenyl; $C_7$-$C_{12}$aralkyl; $C_1$-$C_{12}$heteroalkyl; $C_3$-$C_{12}$cycloheteroalkyl; $C_2$-$C_{11}$heteroaralkyl, $C_6$-$C_{10}$aryl; or $C_1$-$C_9$heteroaryl;

$R_4$ is cyano; $COR_7$, $COOR_7$; $CONR_7R_8$; $SO_2(C_6$-$C_{12})$aryl, $C_2$-$C_{12}$alk-1-enyl; $C_3$-$C_{12}$cycloalk-1-enyl; $C_2$-$C_{12}$alk-1-inyl; $C_2$-$C_{12}$heteroalkyl, $C_3$-$C_5$heterocycloalkyl, $C_6$-$C_{10}$aryl; or $C_1$-$C_9$heteroaryl;

$R_5$ is —$COR_7$; —$COOR_7$; —$OR_7$; —$SR_7$; —$NR_7R_8$; $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; $C_7$-$C_{12}$aralkyl; $C_1$-$C_{12}$alkylphenyl; $C_1$-$C_{12}$alkoxy-$C_6$-$C_{10}$aryl; $C_1$-$C_{12}$heteroalkyl; $C_2$-$C_{11}$heteroaralkyl; $C_3$-$C_{12}$cycloheteroalkyl; $C_6$-$C_{10}$aryl; $C_1$-$C_{12}$alkoxy-$C_6$-$C_{10}$aryl or $C_1$-$C_9$heteroaryl;

$R_6$ is $C_1$-$C_{22}$alkyl; $C_1$-$C_{22}$alkoxy; or $COR_7$;

$R_7$ and $R_8$ independently from each other are hydrogen; $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; $C_7$-$C_{12}$aralkyl; $C_1$-$C_{12}$heteroalkyl; $C_2$-$C_{11}$heteroaralkyl; $C_6$-$C_{10}$aryl; o-$C_6$-$C_{10}$aryl; or $C_1$-$C_9$heteroaryl;

$R_9$ is a $(C_1-C_6)$alkylidene radical; or $R_1$ and $R_2$, $R_1$ and Q, $R_1$ and $R_4$, $R_1$ and $R_6$, $R_2$ and $R_3$, $R_3$ and Q, $R_6$ and Q, T and Q, each independently, are linked together, so that 1, 2, 3 or 4 carbocyclic or N, O and/or S-heterocyclic rings are formed, wherein each of them, independently from each other, may be condensed with an aromatic or heteroaromatic ring, and/or more N-, O- and/or S-heterocycic rings, and each N atom in a N-heterocyclic ring may be substituted by $C_1-C_{22}$alkyl; and n is 1.

3. A method according to claim 2, wherein

Q is —OH; —$OR_6$; or —$NR_7R_8$;

T is —$COR_5$—CN; or —$SO_2$—$(C_6-C_{12})$aryl;

$R_1$ is hydrogen; —$OR_7$, —$SR_7$; —$NR_7R_8$; $C_1-C_{22}$alkyl; $C_2-C_{12}$alkenyl; $C_2-C_{12}$alkinyl; $C_3-C_{12}$cycloalkyl; $C_3-C_{12}$cycloalkenyl; $C_7-C_{12}$aralkyl; or $C_6-C_{10}$aryl;

$R_2$ and $R_3$ independently from each other are $C_1-C_{22}$alkyl; $C_2-C_{12}$alkenyl; $C_2-C_{12}$alkinyl; $C_3-C_{12}$cycloalkyl; $C_3-C_{12}$cycloalkenyl; $C_7-C_{12}$ aralkyl; or $C_6-C_{10}$aryl;

$R_4$ is cyano; —$COR_5$, —$COOR_7$; —$CONR_7R_8$; —$SO_2$ $(C_6-C_{12})$aryl; —$C_1-C_{22}$alkylcarbonylamino-$C_6$-$C_{10}$aryl; or $C_6-C_{10}$aryl;

$R_5$ is —$COR_7$; —$COOR_7$; —$CONR_7R_8$, —$OR_7$, —$SR_7$, —$NR_7R_8$, $C_1-C_{22}$alkyl; $C_2-C_{12}$alkenyl; $C_2-C_{12}$alkinyl; $C_3-C_{12}$cycloalkyl; $C_3-C_{12}$cycloalkenyl; $C_7-C_{12}$aralkyl; $C_6-C_{10}$aryl; or $C_1-C_{12}$alkoxy-$C_6-C_{10}$aryl;

$R_6$, $R_7$ and $R_8$ independently from each other are hydrogen; $C_1-C_{22}$alkyl; $C_3-C_{12}$cycloalkyl; $C_3-C_{12}$cycloalkenyl; $C_7-C_{12}$aralkyl; or $C_6-C_{10}$aryl; or $R_1$ and $R_2$, $R_1$ and Q, $R_1$ and $R_4$, $R_1$ and $R_6$, $R_2$ and $R_3$, $R_3$ and Q, $R_6$ and Q, T and Q are linked together pairwise, so that 1, 2, 3 or 4 carbocyclic or N-, O- and/or S-heterocyclic rings are formed, wherein each of them, independently from each other may be condensed with an aromatic or heteroaromatic ring, and/or more N, O and/or S-heterocycic rings, and each N atom in a N-heterocyclic ring may be substituted by $C_1-C_{22}$alkyl.

4. A method according to claim 2, wherein in formula (1)

$R_1$ is hydrogen; —S—$C_1-C_{22}$alkyl; or $R_1$ and $R_2$, or $R_1$ and $R_4$ together with the linking nitrogen atom form an alkylene radical which my be interrupted by one or more —O— and/or —$NR_7$— or may be condensed with an aromatic ring; and $R_7$ is $C_1-C_{22}$alkyl; $C_3-C_{12}$cycloalkyl; $C_3-C_{12}$cycloalkenyl; $C_7-C_{12}$aralkyl; or $C_6-C_{10}$aryl.

5. A method according to claim 4, wherein in formula (1) $R_1$ is hydrogen.

6. A method according to claim 1, wherein in formula (1)

$R_2$ and $R_3$ independently from each other are $C_1-C_5$alkyl; phenyl-$C_1-C_3$alkyl; hydroxy-$C_1-C_{12}$alkyl; or $R_2$ and $R_3$, or $R_2$ and $R_4$, or $R_2$ and Q together with the linking nitrogen atom form an alkylene radical which may be interrupted by one or more —O— and/or —$NR_7$— or may be condensed with an aromatic ring; and $R_7$ is $C_1-C_{22}$alkyl; $C_3-C_{12}$cycloalkyl; $C_3-C_{12}$cycloalkenyl; $C_7-C_{12}$aralkyl; or $C_6-C_{10}$aryl.

7. A method according to claim 6, wherein $R_2$ and $R_3$ independently from each other are $C_1-C_5$alkyl; or $R_2$ and $R_3$ together with the linking nitrogen atom form a $C_2-C_4$alkylene radical which may be interrupted by —O— or —$NR_7$; and $R_7$ is hydrogen; or $C_1-C_5$alkyl.

8. A method according to claim 1, wherein in formula (1)

$R_4$ is —$COR_5$; phenyl, which is optionally substituted by $C_1-C_5$alkyl; —CN; or —$SO_2$—$(C_6-C_{10})$aryl; or $R_4$ and T together with a bivalent $C_3-C_7$alkylene radical which my be interrupted by one or more —O— and/or —$NR_7$— form a carbocyclic ring which may be condensed with an aromatic ring; and $R_7$ is hydrogen; or $C_1-C_5$alkyl.

9. A method according to claim 8 wherein $R_4$ is —CN; or $COR_5$;

$R_5$ is $C_1-C_{12}$alkyl; or $C_1-C_{12}$alkoxy; or $R_4$ and T together with the bivalent radical of the formula

(1a)

wherein $U_1$ and $U_3$ independently from each other are a radical of formula —$CHR_7$—; —$NHR_7$—; or —O—;

$U_2$ is —$CH_2$; or —CO—; or the direct bond;

$R_7$ is hydrogen; or $C_1-C_{12}$alkyl; form an aromatic ring.

10. A method according to claim 9, wherein T and $R_4$ together with the bivalent radicals selected from

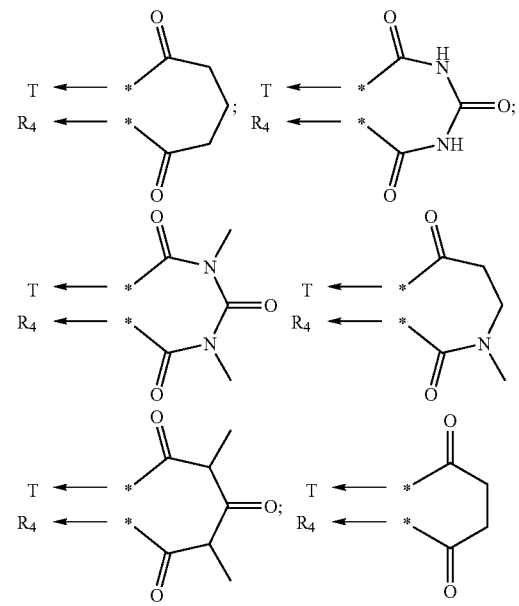

form a heterocyclic ring.

11. A method according to claim 10, wherein in formula (1)

$R_6$ is hydrogen; $C_1-C_5$alkyl; $C_1-C_5$alkoxy; —O—$(C_6$-$C_{10}$aryl); or $R_6$ and Q together with a bivalent $C_3-C_7$alkylene radical which may be interrupted by one or more —O— and/or —$NR_7$— or may be condensed with an aromatic ring, form a heterocyclic ring; and $R_7$ is hydrogen; or $C_1C_{12}$alkyl.

12. A method according to claim 11, wherein $R_6$ is hydrogen.

13. A method according to claim 1, wherein in formula (1)

T is —CN; —$COR_5$; or —$SO_2$-phenyl;

$R_5$ is $C_1-C_5$alkyl; $C_1-C_5$alkoxy; or $NR_7R_8$;

$R_7$ and $R_8$ independently from each other are hydrogen; or $C_1$-$C_5$alkyl; or T and Q together with the bivalent $C_3$-$C_7$alkylene radical which may be interrupted by one or more —O— and/or —$NR_7$— or may be condensed with an aromatic ring, form a heterocyclic ring.

14. A method according to claim 13, wherein

T is —CN; or —$COR_5$; and $R_5$ is $C_1$-$C_5$alkyl; or $C_1$-$C_5$alkoxy.

15. A method according to claim 1, wherein

Q is hydroxy; $C_1$-$C_5$alkoxy; or —$NR_7R_8$; and $R_7$ and $R_8$ independently from each other are hydrogen; $C_1$-$C_5$alkyl; or phenyl, which may be substituted by one or more $C_1$-$C_5$alkyl or $C_1$-$C_5$alkoxy groups.

16. A method according to claim 15, wherein

Q is hydroxy.

17. A method according to claim 1, which comprises compounds of formula

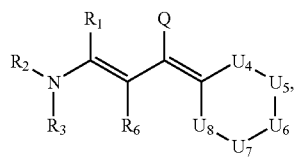

(2)

wherein $U_4$, $U_5$, $U_6$, $U_7$ and $U_8$ independently of each other are —$CHR_5$—; —CO—; —$NR_7$—; —CS—; or —O—;

$R_5$ is hydrogen; or $C_1$-$C_5$alkyl; and $R_1$, $R_2$, $R_3$, $R_6$, $R_7$ and Q are defined as in claim 1.

18. A method according to claim 1, which comprises compounds of formula

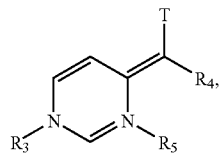

(3)

wherein $R_5$ is hydrogen; or $C_1$-$C_5$alkyl; and $R_3$, $R_4$, and T are defined as in claim 1.

19. A method according to claim 18, which comprises compounds of formula (3), wherein $R_3$ is $C_1$-$C_{22}$alkyl; $C_6$-$C_{10}$aryl; or $C_7$-$C_{12}$aralkyl.

20. A method according to claim 18, which comprises compounds of formula (3), wherein $R_3$ is $C_6$-$C_{10}$aryl.

21. A method according to claim 1, wherein at least one of the radicals $R_1$, $R_6$ or Q is different from hydrogen.

22. A method according to claim 1 wherein

Q is hydrogen; or $C_1$-$C_{22}$alkyl;

T is —$COR_5$; —CN; or —$SO_2$—$(C_6$-$C_{12})$aryl;

$R_1$ is hydrogen; or $C_1$-$C_{22}$alkyl;

$R_2$ and $R_3$ independently from each other are $C_1$-$C_{22}$alkyl;

$R_4$ is CN; $COR_5$; $CONH_2$; or $SO_2(C_6$-$C_{12})$aryl, $R_5$ is —$OR_7$; —$SR_7$, —$NHR_7$, —$NR_7R_8$; $C_1$-$C_{22}$alkyl; $C_7$-$C_{12}$aralkyl;

$R_7$ and $R_8$ independently from each other are hydrogen; $C_1$-$C_{22}$alkyl; —$(CH_2)_m$—Si—$R_{10}R_{11}R_{12}$; Si$(OR_{10})(OR_{11})(OR_{12})$; Si$R_{10}(OR_{11})(OR_{12})$; Si$R_{10}R_{11}(OR_{12})$, or a radical X-Sil;

$R_9$ is a $(C_1$-$C_6)$alkylidene radical;

$R_{10}$, $R_{11}$, $R_{12}$ independently from each other are $C_1$-$C_{22}$alkyl;

X is a linker;

Sil is a silane-, oligosiloxane- or polysiloxane radical;

$R_1$ and $R_2$, $R_1$ and Q, $R_1$ and $R_6$, $R_1$ and T, $R_2$ and $R_3$, $R_2$ and $R_4$, $R_2$ and $R_6$, $R_2$ and Q, $R_4$ and $R_6$, $R_4$ and T, $R_6$ and Q, T and Q, each independently, are linked together, so that 1, 2, 3 or 4 carbocyclic or N, O and/or S-heterocyclic rings are formed, wherein each of them, independently from each other, may be condensed with an aromatic or heteroaromatic ring, and/or more N-, O-and/or S-heterocycic rings, and each N atom in a N-heterocyclic ring may be substituted by $C_1$-$C_{22}$alkyl;

n is a number from 1 to 4; and m is a number for 0 to 4; wherein at least one of the radicals $R_1$, $R_6$ or Q is different from hydrogen.

23. A method according to claim 22, wherein $R_1$, $R_6$ and Q, independently from each other are hydrogen; or $C_1$-$C_{22}$alkyl, wherein at least one of $R_1$, $R_6$ and Q is different from hydrogen.

24. A method according to claim 23, wherein $R_1$, $R_6$ and Q, independently from each other are hydrogen; or $C_1$-$C_5$alkyl, wherein at least one of $R_1$, $R_6$ and Q is different from hydrogen.

25. A method according to claim 22, wherein

T and $R_4$ independently from each other are —$COR_5$; —CN; or —$SO_2$—$(C_6$-$C_{12})$aryl; and $R_5$ is —$OR_7$; —$NR_7R_8$; $C_1$-$C_{22}$alkyl; $C_7$-$C_{12}$aralkyl;

$R_7$ and $R_8$ independently from each other are hydrogen; $C_1$-$C_{22}$alkyl; —$(CH_2)_m$—Si—$R_{10}R_{11}R_{12}$; and $R_{10}$, $R_{11}$, and $R_{12}$ independently from each other are $C_1$-$C_{22}$alkyl.

26. A method according to claim 25, wherein

T and $R_4$ independently from each other are —CN; $SO_2C_6H_5$;

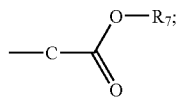

or a radical of formula

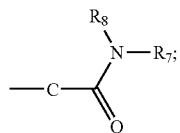

wherein $R_7$ and $R_8$, independently from each other are $C_1$-$C_{12}$alkyl; or a radical of formula —$SiR_{10}R_{11}R_{12}$; and $R_{10}$, $R_{11}$ and $R_{12}$ are $C_1$-$C_5$alkyl.

27. Monomeric and polymeric compounds having the structural element of formula

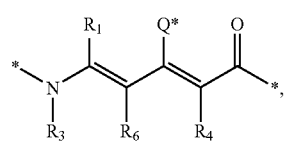

(4)

wherein at least one of the asterix-marked radicals are joint with the monomeric or polymeric radical; and $R_1$, $R_2$, $R_4$ and $R_6$ are defined as in claim (1).

* * * * *